United States Patent
Herron et al.

(10) Patent No.: US 7,449,457 B2
(45) Date of Patent: Nov. 11, 2008

(54) SUBSTITUTED HETEROCYCLIC CARBOXAMIDES WITH ANTITHROMBOTIC ACTIVITY

(75) Inventors: David Kent Herron, Indianapolis, IN (US); Sajan Joseph, Indianapolis, IN (US); Angela Lynn Marquart, Greenwood, IN (US); John Joseph Masters, Fishers, IN (US); David Mendel, Indianapolis, IN (US); Gerald Floyd Smith, Greenwood, IN (US); Anne Louise Tebbe, Hamburg (DE); Philip Parker Waid, Indianapolis, IN (US); Michael Robert Wiley, Indianapolis, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 777 days.

(21) Appl. No.: 10/497,250

(22) PCT Filed: Dec. 2, 2002

(86) PCT No.: PCT/US02/36139

§ 371 (c)(1),
(2), (4) Date: May 28, 2004

(87) PCT Pub. No.: WO03/050088

PCT Pub. Date: Jun. 19, 2003

(65) Prior Publication Data

US 2004/0242581 A1  Dec. 2, 2004

Related U.S. Application Data

(60) Provisional application No. 60/338,337, filed on Dec. 7, 2001.

(51) Int. Cl.
 *A61K 31/54* (2006.01)
 *A61K 31/44* (2006.01)
 *A61K 31/535* (2006.01)
 *C07D 417/00* (2006.01)
 *C07D 413/00* (2006.01)
 *C07D 401/00* (2006.01)

(52) U.S. Cl. .................. 514/227.8; 514/237.2; 514/333; 514/253.13; 544/60; 544/111; 544/365; 546/256

(58) Field of Classification Search .................. 544/60, 544/111, 365; 514/227.8, 237.2, 333, 253.13; 546/256
See application file for complete search history.

(56) References Cited

U.S. PATENT DOCUMENTS 6,376,515 B2   4/2002  Zhu et al.
6,794,380 B2 *  9/2004  Brown ........................ 514/183
2002/0002183 A1   1/2002  Zhu et al.

FOREIGN PATENT DOCUMENTS

| EP | 0 385 350 A1 | 9/1990 |
|---|---|---|
| EP | 0 385 351 A1 | 9/1990 |
| EP | 1 031 563 A1 | 8/2000 |
| EP | 1 273 575 A1 | 1/2003 |
| WO | WO 95/25723 | 9/1995 |
| WO | WO 98/54164 | 12/1998 |
| WO | WO 99/00121 | 1/1999 |
| WO | WO 99/00126 | 1/1999 |
| WO | WO 99/00127 | 1/1999 |
| WO | WO 99/00128 | 1/1999 |
| WO | WO 99/32477 | 7/1999 |
| WO | WO 00/39092 | 7/2000 |
| WO | WO 00/39111 | 7/2000 |
| WO | WO 00/39117 | 7/2000 |
| WO | WO 00/39118 | 7/2000 |
| WO | WO 01/19788 | 3/2001 |
| WO | WO 01/19798 | 3/2001 |
| WO | WO 01/64642 | 9/2001 |
| WO | WO 01/64643 | 9/2001 |
| WO | WO 01/74791 | 10/2001 |
| WO | WO 02/10154 | 2/2002 |
| WO | WO 02/14308 | 2/2002 |
| WO | WO 02/064567 | 8/2002 |

OTHER PUBLICATIONS

U.S. Appl. No. 60/154,332, filed Mar. 2001, Zhu et al.
U.S. Appl. No. 60/185,746, filed Mar. 2001, Zhu et al.
U.S. Appl. No. 09/663,420, filed Sep. 2001, Zhu et al.

* cited by examiner

*Primary Examiner*—Janet L. Andres
*Assistant Examiner*—Binta M Robinson
(74) *Attorney, Agent, or Firm*—Thomas E. Jackson

(57) ABSTRACT

This application relates to a compound of formula (I) (or a pharmaceutically acceptable salt thereof) as defined herein, pharmaceutical compositions thereof, and its use as an inhibitor of factor Xa, as well as a process for its preparation and intermediates therefor.

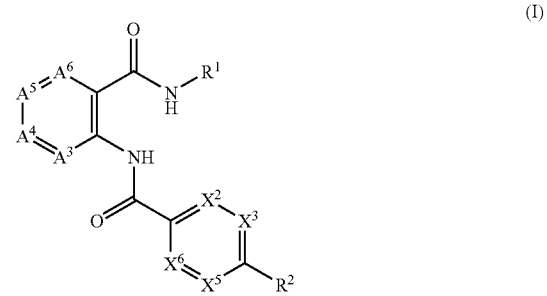

11 Claims, No Drawings

SUBSTITUTED HETEROCYCLIC CARBOXAMIDES WITH ANTITHROMBOTIC ACTIVITY

This application claims the benefit of U.S. Provisional Application No. 60/338,337, filed Dec. 7, 2001, which is incorporated by reference herein.

This invention relates to anticoagulant substituted heterocyclic carboxamides which demonstrate activity as inhibitors of factor Xa and, accordingly, which are useful antithrombotics in mammals. In particular it relates to substituted heterocyclic carboxamides having high anticoagulant activity, and antithrombotic activity. Thus, this invention relates to new substituted heterocyclic carboxamides which are inhibitors of factor Xa, pharmaceutical compositions containing the substituted heterocyclic carboxamides as active ingredients, and the use of the substituted heterocyclic carboxamides as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the substituted heterocyclic carboxamides are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6-24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, for example, B. Y. Zhu and R. M. Scarborough, *Annual Reports in Medicinal Chemistry*, (2000), 35, 83-102, Factor Xa Inhibitors: Recent Advances in Anticoagulant Agents.

Although the heparins and coumarins are effective anticoagulants, there still exists a need for anticoagulants which act selectively on factor Xa or thrombin, and which, independent of antithrombin III, exert inhibitory action shortly after administration, preferably by an oral route, and do not interfere with lysis of blood clots, as required to maintain hemostasis.

The present invention is directed to the discovery that the substituted heterocyclic amides of the present invention, as defined below, are potent inhibitors of factor Xa which may have high bioavailability following oral administration.

According to the invention there is provided a compound of formula I

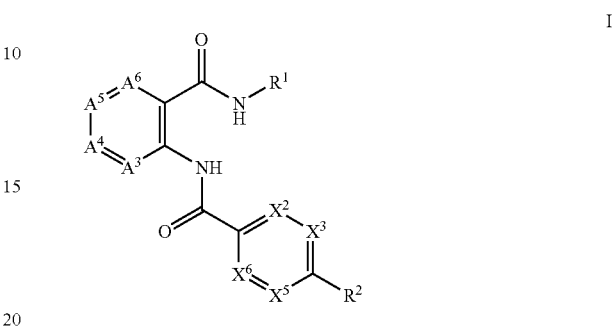

or a pharmaceutically acceptable salt thereof, wherein $A^3$, $A^4$, $A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$; wherein $R^3$ is hydrogen, fluoro, chloro, methyl, methoxy, hydroxy or carboxy;

one of $R^4$ and $R^5$ is hydrogen, (1-4C)alkyl, halo, trifluoromethyl, trifluoromethoxy, cyano, hydroxymethyl, (1-3C) acyl, $R^fO$—, $R^fO_2C$—, $R^fO_2C$—$CH_2$—, $R^fO_2C$—$CH_2$—O—, methylthio or $R^gNH$—;

the other of $R^4$ and $R^5$ is hydrogen, halo or methyl; and $R^6$ is hydrogen, fluoro, chloro, methyl or methoxy;

in which $R^f$ is hydrogen, (1-4C)alkyl or benzyl; $R^g$ is hydrogen, (1-3C)acyl, trifluoroacetyl, methoxyacetyl, or $R^hSO_h$— (wherein h is 1 or 2); and $R^h$ is (1-4C)alkyl, trifluoromethyl, phenyl, amino, methylamino or dimethylamino; or $A^3$, $A^4$, $A^5$ and $A^6$, together with the two carbons to which they are attached, complete a substituted pyridine ring in which one of $A^3$, $A^4$, $A^5$ and $A^6$ is N, and each of the others is $CR^3$, $CR^4$, $CR^5$ or $CR^6$, respectively; wherein each of $R^3$, $R^4$, $R^5$ and $R^6$ is independently hydrogen or methyl, or one of $R^3$, $R^4$, $R^5$ and $R^6$ attached to a carbon which is not bonded to an N-atom is chloro and the others are hydrogen;

$R^1$ is 2-pyridinyl (which may bear a methyl, methoxy, methylthio, fluoro or chloro substituent at the 5-position), or $R^1$ is 3-pyridinyl (which may bear a methyl, fluoro or chloro substituent at the 6-position), or $R^1$ is phenyl (which may bear one, two or three substituents at the 3-, 4- or 5-position(s) independently selected from halo, cyano, carbamoyl, methyl, methoxy, difluoromethoxy, hydroxymethyl, formyl, vinyl, amino, hydroxy and 3,4-methylenedioxy; and in addition-the phenyl may bear a 2-chloro or 2-fluoro substituent), or $R^1$ is 6-indolyl (which may bear a chloro or methyl substituent at the 3-position);

one or two of $X^2$, $X^3$, $X^5$ and $X^6$ is N; and each of the others of $X^2$, $X^3$, $X^5$ and $X^6$ is CH; and $R^2$ is phenyl, substituted phenyl {which bears one or more substituents independently selected from amino, methoxy, halo and (1-4C)alkyl}, a 5- or 6-membered heteroaryl group {having one or two heteroatoms selected from oxygen, sulfur and nitrogen}, (1-4C)alkoxy, $R^qSO_q$— {wherein q is 0, 1 or 2; and $R^q$ is (1-4C)alkyl}, or —$NR^sR^t$ in which $R^s$ and $R^t$ are independently hydrogen or (1-4C)alkyl, or $R^s$ is hydrogen and $R^t$ is hexahydro-2-oxoazepin-3-yl or 1-azabicyclo[2.2.2]oct-3-yl, or —$NR^sR^t$ is pyrrolidin-1-yl, piperidin-1-yl, morpholin-4-yl, thiomorpholin-4-yl, piperazin-1-yl or 3-oxopiperazin-1-yl wherein pyrrolidin-1-yl or piperidin-1-yl may bear a substituent $R^u$ at the 3- or 4-position and piperazin-1-yl may bear a substituent $R^v$ at the 4-position in which $R^u$ is amino, aminocarbonyl, aminomethyl, hydroxy or hydroxymethyl and $R^v$ is (1-3C)alkyl, formyl or 2-hydroxyethyl.

As used herein, the expression a compound of formula I or the expression a compound of the invention includes the compound and any conventional prodrug thereof, as well as a pharmaceutically acceptable salt of said compound or prodrug.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against factor Xa, it being well known in the art how to prepare or isolate particular forms and how to determine inhibitory properties against factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

A prodrug of a compound of formula I may be one formed in a conventional manner with a functional group of the compound, such as with an amino, hydroxy or carboxy group.

Particular values are listed below for radicals, substituents, and ranges, for illustration only, and they do not exclude other defined values or other values within defined ranges for the radicals and substituents. Thus, a particular value for halo is fluoro, chloro or bromo; for (1-3C)alkyl is methyl, ethyl, propyl or isopropyl; for (1-4C)alkyl, alone or as part of a (1-4C)alkoxy, is methyl, ethyl, propyl, isopropyl, butyl, isobutyl or t-butyl; for (1-3C)acyl is formyl, acetyl or propionyl; and for a 5- or 6-membered heteroaryl group is 4-pyridyl.

One particular compound of formula I is one wherein $A^3$, $A^4$, $A^5$ and $A^6$, together with the two carbons to which they are attached, complete a substituted benzene.

A more particular compound, or salt thereof, as described above is one wherein each of $R^3$, $R^4$ and $R^6$ is hydrogen; and $R^5$ is fluoro or chloro.

Another particular compound of formula I is one wherein $A^3$, $A^4$, $A^5$ and $A^6$, together with the two carbons to which they are attached, complete a substituted pyridine; and, more particularly wherein $A^6$ is N, $R^3$ and $R^4$ are each hydrogen, and $R^5$ is hydrogen or methyl.

For a compound of formula I as described herein, a particular value for $R^1$ is 2-pyridinyl which bears a methyl, fluoro or chloro substituent at the 5-position.

For a compound of formula I as described herein, one particular value for $R^2$ is methoxy, methylthio or methylsulfinyl.

For a compound of formula I as described herein, another particular value for $R^2$ is —$NR^sR^t$; and, more particularly, wherein —$NR^sR^t$ is pyrrolidin-1-yl, 3-amino-pyrrolidin-1-yl, 3-hydroxypyrrolidin-1-yl, 3-hydroxy-piperidin-1-yl, morpholin-4-yl, 4-methylpiperazin-1-yl or 4-isopropylpiperazin-1-yl; and, especially, wherein —$NR^sR^t$ is 3-aminopyrrolidin-1-yl or 3-hydroxypyrrolidin-1-yl.

For a compound of formula I as described herein, a particular compound, or salt thereof, is one wherein $X^2$ is N and each of $X^3$, $X^5$ and $X^6$ is CH; or
$X^3$ is N and each of $X^2$, $X^5$ and $X^6$ is CH; or
each of $X^2$ and $X^3$ is N; and each of $X^5$ and $X^6$ is CH; or
each of $X^2$ and $X^5$ is N; and each of $X^3$ and $X^6$ is CH; or
each of $X^2$ and $X^6$ is N; and each of $X^3$ and $X^5$ is CH.

A more particular compound of formula I is one wherein $A^3$, $A^4$, $A^5$ and $A^6$, together with the two carbons to which they are attached, complete a substituted benzene;

each of $R^3$, $R^4$ and $R^6$ is hydrogen; and $R^5$ is fluoro or chloro;

$R^1$ is 2-pyridinyl which bears a fluoro-or chloro substituent at the 5-position;

$R^2$ is phenyl, methoxy, methylthio, methylsulfinyl, (hexahydro-2-oxoazepin-3-yl)amino, (1-azabicyclo[2.2.2]oct-3-yl)amino, pyrrolidin-1-yl, 3-aminopyrrolidin-1-yl, 3-hydroxypyrrolidin-1-yl, 3-aminocarbonylpiperidin-1-yl, 3-hydroxypiperidin-1-yl, 3-hydroxymethylpiperidin-1-yl, morpholin-4-yl, thiomorpholin-4-yl, piperazin-1-yl, 4-methylpiperazin-1-yl, 4-isopropylpiperazin-1-yl, 4-formyl-piperazin-1-yl, 4-(2-hydroxyethyl)piperazin-1-yl, or 3-oxopiperazin-1-yl; and $X^2$ is N and each of $X^3$, $X^5$ and $X^6$ is CH; or
$X^3$ is N and each of $X^2$, $X^5$ and $X^6$ is CH; or
each of $X^2$ and $X^3$ is N; and each of $X^5$ and $X^6$ is CH; or
each of $X^2$ and $X^5$ is N; and each of $X^3$ and $X^6$ is CH; or
each of $X^2$ and $X^6$ is N; and each of $X^3$ and $X^5$ is CH.

A specific compound, or pharmaceutically acceptable salt thereof, is any one of those provided in the Examples, especially that of Example 6 or 8.

A pharmaceutically acceptable salt of a compound of the instant invention is one which is the acid addition salt of a basic compound of formula I with an inorganic or organic acid which affords a physiologically acceptable anion or which is the salt formed by an acidic compound of formula I with a base which affords a physiologically acceptable cation and provides a particular aspect of the invention.

As an additional aspect of the invention there is provided a pharmaceutical composition comprising in association-with a pharmaceutically acceptable carrier, diluent or excipient, a compound of formula I, or a pharmaceutically acceptable salt thereof, as provided in any of the descriptions herein.

In addition, there is provided the use of a compound of formula I, or a pharmaceutically acceptable salt thereof, as described herein as an active ingredient in the manufacture of a medicament for use in producing an anticoagulant or antithrombotic effect.

The present invention also provides a method of inhibiting coagulation in a mammal comprising administering to a mammal in need of treatment, a coagulation inhibiting dose of a compound of formula I, or a pharmaceutically acceptable salt thereof, having any of the definitions herein.

The present invention further provides a method of inhibiting factor Xa comprising administering to a mammal in need of treatment, a factor Xa inhibiting dose of compound of formula I having any of the definitions herein.

Further, the present invention provides a method of treating a thromboembolic disorder comprising administering to a mammal in need of treatment, an effective dose of a compound of formula I, or a pharmaceutically acceptable salt thereof, having any of the definitions herein.

Also, there is provided a compound of formula I, or a pharmaceutically acceptable salt thereof, having any of the definitions herein for use as an antithrombotic agent.

In addition, there is provided the use of a compound of formula I, or a pharmaceutically acceptable salt thereof, having any of the definitions herein for the manufacture of a medicament for treatment of a thromboembolic disorder.

As an additional feature of the invention there is provided a pharmaceutical composition comprising in association with a pharmaceutically acceptable carrier, diluent or excipient, a prodrug of a compound of formula I, or a pharmaceutically acceptable salt thereof, as provided in any of the descriptions herein.

A compound of formula I may be prepared by processes which include processes known in the chemical art for the production of structurally analogous compounds or by a novel process described herein. A novel process described herein provides another aspect of the invention. A process for the preparation of a compound of formula I (or a pharmaceutically acceptable salt thereof) and novel intermediates for the manufacture of a compound of formula I provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a compound of formula I, or a pharmaceutically acceptable salt thereof, as provided in any of the above descriptions, which comprises:

(A) for a compound of formula I in which $R^2$ is (1-4C)alkoxy, (1-4C)alkylthio or —$NR^sR^t$, substituting the group $Y^a$ of a compound of formula II,

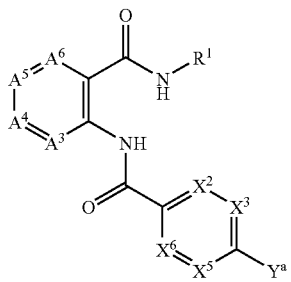

II in which $Y_a$ is a leaving group for nucleophilic aromatic substitution, using a (1-4C)alkanol or (1-4C)alkoxide, a (1-4C)alkylthioxide, or an amine of formula H—$NR^sR^t$, respectively;

(B) for a compound of formula I in which $R^2$ is phenyl, substituted phenyl or a 5- or 6-membered heteroaryl group, cross coupling a compound of formula III,

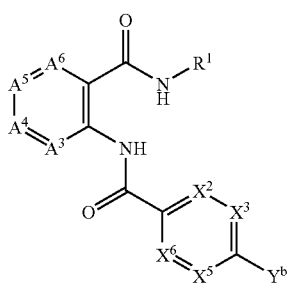

III in which $Y^b$ is halo or trifluoromethylsulfonyloxy, with a corresponding reagent of formula $Y^c$—$R^2$, in which $Y^c$ represents a boron or tin cross-coupling residue in the presence of a cross-coupling catalyst;

(C) for a compound of formula I in which $R^2$ is (1-4C)alkylsulfinyl or (1-4C)alkylsulfonyl, oxidizing a corresponding compound of formula I in which $R^2$ is (1-4C)alkylthio or (1-4C)alkylsulfinyl, respectively;

(D) acylating an amine of formula $H_2N$—$R^1$, or a deprotonated derivative thereof, using an acid of formula IV or an activated derivative thereof,

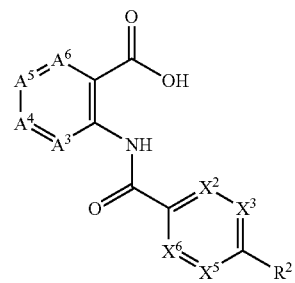

IV or (E) acylating an amine of formula VI,

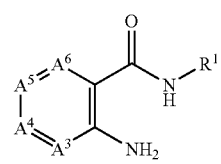

VI using an acid of formula VII,

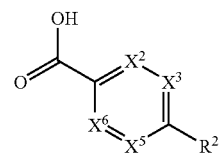

VII or an activated derivative thereof, whereafter, for any of the above procedures, when a functional group of a starting material is protected using a protecting group, removing the protecting group;

whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure;

and wherein, unless otherwise specified, $A^3$-$A^6$, $R^1$-$R^2$, $X^2$-$X^3$ and $X^5$-$X^6$ have any of the values defined in any of the above descriptions.

As used herein, a leaving group "$Y^a$" is a moiety which is displaced in an aromatic (or heteroaromatic) nucleophilic substitution reaction, for example a halo group (such as fluoro or chloro), an alkoxy group (such as methoxy), a sulfonate ester group (such as methylsulfonyloxy, p-toluyl-sulfonyloxy or trifluoromethylsulfonyloxy), or the reactive species derived from treating an alcohol with triphenyl-phospine, diethyl azodicarboxylate and triethyl amine (in a Mitsunobu reaction). The substitution may be carried out by heating a mixture of the reagents in a polar solvent, for example in dimethyl sulfoxide in a sealed tube as described at Example 2, or for examples as described at Example 23.

For a carboxylic acid, a typical activated derivative includes an ester (particularly a lower alkyl ester such as the methyl or ethyl ester), an acid halide (particularly the acid chloride), and an activated ester or anhydride (including the 4-nitrophenyl ester and an activated ester or anhydride derived from a coupling reagent), as well as (when the product is a urea) the isocyanate. Typical procedures include those described for preparation of intermediate compounds at Intermediate A-1.

Typical values for $Y^c$ as a boron or tin cross-coupling residue include —B(OH)$_2$ (for which a typical cross-coupling catalyst includes tetrakistriphenylphosphine palladium, see Example 1) or —Sn(CH$_3$)$_2$ (for which a typical cross-coupling catalyst is a Stille catalyst). Conditions suitable for a Stille cross coupling and conventional values for a Stille catalyst, conveniently denoted as a palladium(0) catalyst, are known to those of skill in the art.

For a compound of formula I in which one of of $R^4$ and $R^5$ is $R^g$NH— and $R^g$ is $R^h$SO$_h$— (wherein h is 1 or 2), a conventional procedure for substituting the nitrogen of a compound in which $R^g$ is hydrogen comprises treating the amine with the requisite sulfinyl or sulfonyl halide, for example using the chloride of formula $R^h$SO$_h$—Cl.

A novel intermediate or starting material compound provides a further aspect of the invention. The various starting materials may be made by processes which include processes known in the chemical art for the production of structurally analogous compounds or by a novel process described herein or one analogous thereto.

Thus, one particular intermediate is an acid of formula VII,

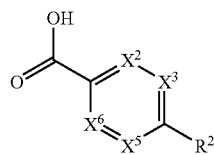

VII or an activated derivative thereof, or a salt of the acid or activated derivative, in which $X^2$-$X^3$, $X^5$-$X^6$ and $R^2$ have any of the values defined herein, or a derivative thereof in which a functional group other than the carboxy group, or activated derivative thereof, is protected using a protecting group.

Another intermediate is an acid of formula IV,

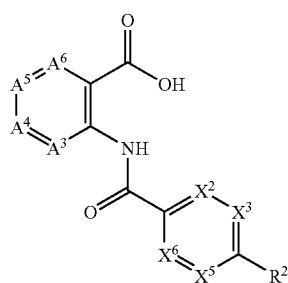

IV or an activated derivative thereof, or a salt of the acid or activated derivative, in which $A^3$-$A^6$, $X^2$-$X^3$, $X^5$-$X^6$ and $R^2$ have any of the values defined herein, or a derivative thereof in which a functional group other than the carboxy group, or activated derivative thereof, is protected using a protecting group.

For an acid of formula IV, a particular activated derivative is a compound of formula V,

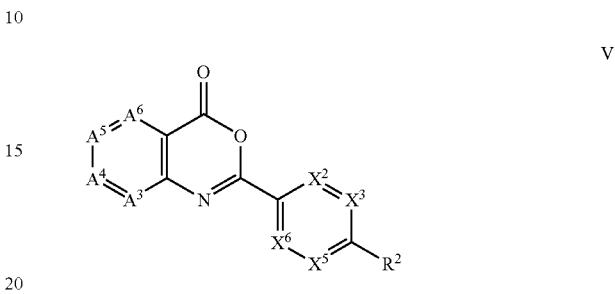

V or a salt of the active derivative, in which $A^3$-$A^6$, $X^2$-$X^3$, $X^5$-$X^6$ and $R^2$ have any of the values defined herein, or a derivative thereof in which a functional group other than the activated derivative of the carboxy group is protected using a protecting group.

As a further aspect of the invention, there is provided the use of a compound (or activated and/or protected derivative thereof or salt of the compound or derivative) of formula IV or VII as a starting material in the preparation of an inhibitor of factor Xa.

As mentioned above, a compound corresponding to a compound of formula I but in which a functional group is protected may serve as an intermediate for a compound of formula I. Accordingly, such a protected intermediate for a novel compound of formula I provides a further aspect of the invention. Thus, as one particular aspect of the invention, there is provided a compound corresponding to a novel compound of formula I as defined above in which there is a hydroxy, but in which the corresponding substituent is —OP$^P$ in place of hydroxy, wherein P$^P$ is a phenol protecting group other than methyl. Phenol protecting groups are well known in the art, for example as described in T. W. Greene and P. G. M. Wuts, "Protecting Groups in Organic Synthesis" (1991). Further, P$^P$ may denote a functionalized resin, for example as disclosed in H. V. Meyers, et al., *Molecular Diversity*, (1995), 1, 13-20.

As mentioned above, the invention includes a pharmaceutically acceptable salt of the factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt.

If not commercially available, a necessary starting material for the preparation of a compound of formula I may be prepared by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of substitution, protection and deprotection are well known in the art for preparation of a compound such as one of formulae II-VII.

Generally, a basic compound of the invention is isolated best in the form of an acid addition salt. A salt of a compound of formula I formed with an acid such as mentioned above is useful as a pharmaceutically acceptable salt for administration of the antithrombotic agent and for preparation of a pharmaceutical composition of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions,* John Wiley & Sons, 1981.

The compounds of the invention are believed to selectively inhibit factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting factor Xa in a mammal comprising administering to a mammal in need of treatment an effective (factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The factor Xa inhibition, coagulation inhibition and thromboembolic disorder treatment contemplated by the present method includes both medical therapeutic and/or prophylactic treatment as appropriate.

In a further embodiment, the invention relates to treatment, in a human or animal, of a condition where inhibition of factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction.

Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs, including joint replacement, and cardiac valves. Further, the compounds have expected utility in anticoagulant treatment in hemodialysis and disseminated intravascular coagulation. Further, the compounds may be useful in reducing the increased thrombin generation which occurs in the airways of patients with asthma; see, E. C. Gabazza, et al., *Lung,* (1999), 177(4), 253-262. A further expected utility is in rinsing or coating of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises an effective factor Xa inhibiting amount of a compound of formula I in association with a pharmaceutically acceptable carrier, excipient or diluent.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art.

The ability of a compound of the present invention to be an effective and orally active factor Xa inhibitor may be evaluated in one or more of the following assays or in other standard assays known to those in the art.

The inhibition by a compound of the inhibition of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265-300. The inhibitor binding affinity is measured as apparent association constant Kass which is the hypothetical equilibrium constant for the reaction between enzyme and the test inhibitor compound (I).

$$Kass = \frac{[Enzyme - I]}{([Enzyme] \times [I])}$$

Conveniently, enzyme inhibition kinetics are performed in a high-volume protocol using automated dilutions of inhibitors (n=3 for each of four to eight inhibitor concentrations) into 96-well polystyrene plates and reaction rates are determined from the rate of hydrolysis of appropriate p-nitroanilide substrates at 405 nm using a Thermomax plate reader from Molecular Devices (San Francisco, Calif.). The same general protocol is followed for all enzymes studied: In each well is placed 50 µL buffer (0.06 M Tris, 0.3 M NaCl, pH 7.4), followed by 25 µL of inhibitor solution (in 100% methanol) and 25 µL enzyme solution (e.g., human factor Xa, 32 nM in 0.03 M Tris, 0.15 M NaCl, 1 mg/mL HAS); finally, within two minutes, 150 µL aqueous solution of chromogenic substrate (e.g., 0.3 mM BzIle-Glu-Gly-Arg-pNA) is added to start the enzymatic reaction. Final factor Xa concentration is 3.2 nM. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, human factor Xa is used to hydrolyze BzIle-Glu-Gly-Arg-pNA; 5.9 nM human thrombin is used to hydrolyze 0.2 mM BzPhe-Val-Arg-pNA; 3.4 nM human plasmin is used with 0.5 mM HD-Val-Leu-Lys-pNA; 1.2 nM human nt-PA is used with 0.8 mM HD-Ile-Pro-Arg-pNA; and 0.4 nM urokinase is used with 0.4 mM pyro-Glu-Gly-Arg-pNA.

Kass is calculated for a range of concentrations of test compounds which produce hydrolysis inhibition of between 20% and 80% of control and the mean value reported in units of liter per mole. In general, a factor Xa inhibiting compound of formula I of the instant invention, as exemplified herein, exhibits a Kass of $3-10 \times 10^6$ L/mole or greater.

The factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.*, 185, 1-11 (1980; and Smith, et al., *Biochemistry*, 11, 2958-2967, (1972). Human fibrinogen (98 percent pure/plasmin free) is from American Diagnostica, Greenwich, Connecticut. Radiolabeling of fibrinogen I-2 preparations is performed as previously reported. Smith, et al., *Biochemistry*, 11, 2958-2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1-11 (1980); and Smith, et al., *Biochemistry*, 11, 2958-2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163-174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay. Compounds of the instant invention potently extended the prolongation times in the APTT and PT assays, for example in some cases, with assay concentrations necessary to double the APPT or PT of less than 10 µM.

Animals

Male Sprague Dawley rats (350-425 gm, Harlan Sprague Dawley Inc., Indianapolis, Ind.) are anesthetized with xylazine (20 mg/kg, s.c.) and ketamine (120 mg/kg, s.c.) or preferably are anesthetized using isoflurane anesthesia (2-3%, conveniently 2.5%, for surgery; 1.5-2.5%, conveniently 2.5%, for maintenance; flow rate kept at 0.5% throughout) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, Br J Pharmacol, 77:29, 1982).

FeCl3 Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 µL is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, Thromb. Res., 60:269, 1990).

Ex Vivo Coagulation Parameters

Ex vivo plasma thrombin time (TT), prothrombin time (PT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with isotonic saline (0.1 mL) and bovine thrombin (0.1 mL, 30 U/mL in TRIS buffer; Parke Davis) at 37° C. For PT, to plasma (0.1 mL) mixed with isotonic saline (0.1 mL) is added PT reagent (0.1 mL, Dade, Thromboplastin-C); and the fibrometer started immediately after the addition of the final reagent. For APTT, plasma (0.1 mL) and APTT solution (0.1 mL, organon Teknika) are incubated for 5 minutes (37° C.); and $CaCl_2$ (0.1 mL, 0.025 M) is added to start coagulation. Assays are done in duplicate and averaged.

Index of Bioavailability

Bioavailability studies may be conducted as follows. Compounds are administered as aqueous solutions, or as solutions in 5% PEG 200, to male Fisher rats, intravenously (iv) at 5 mg/kg via tail vein injection and orally (po) as aqueous solutions, or as a suspension in 5% acacia, to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varian) cartridges for sample preparation and a methanol/30 nM ammonium acetate buffer (pH 4) gradient optimized for each compound. % Oral bioavailability is calculated by the following equation:

$$\% \text{ Oral bioavailability} = \frac{\text{AUC po}}{\text{AUC iv}} \times \frac{\text{Dose iv}}{\text{Dose po}} \times 100$$

where AUC is area under the curve calculated from the plasma level of compound over the time course of the experiment following oral (AUC po) and intravenous (AUC iv) dosing.

Compounds

For oral determinations, the compound may be administered orally, by gavage, as a suspension in 5% acaia to conscious fasted rats. The pretreatment time before flow is established through the shunt is selected based upon the peak apparent plasma concentration recorded in preliminary time course experiments that track apparent drug concentration in plasma following oral administration to conscious fasted rats, and typically varies between 1 to 5 hours. Animals used in antithrombotic efficacy experiments are anesthetized as described 15 minutes befoe the predetermined pretreatment time to allow for surgical preparation of the animals. Compound solutions are prepared fresh daily in normal saline or in 5% PEG200 in water for iv determinations and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Typically, bolus injection volume is 1 mL/kg for iv, and 5 mL/kg for po, and infusion volume is 3 mL/h. For a similar procedure run in the anesthesized rabbit, for example an infusion rate of 6.8 mL/h was used for one compound infused in 5% PEG200 in water.

Statistics

Results are expressed as means+/– SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months-2 years; 12-13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66-74° F.; 45-50 percent relative humidity; and lighted from 0600-1800 hours.

Pharmacokinetic Model.

Test compound is formulated immediately prior to dosing by making a suspension in a "wet granulaion" (povidone, 0.85 mg/mL; lactose, 15.0 mg/mL; and polysorbate 80, 65 µL in 250 mL water). Dogs are given a single 20 mg/kg (in 25 mL of wet granulation) dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total-clearance, Clt; volume of distribution, VD; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Male dogs (Beagles, as described above) are fasted overnight and dosed with test compound that is formulated immediately prior to dosing by making a suspension in a "wet granulation" as described above. Dogs are given a single dose of 5, 10 or 20 mg/kg (in 25 mL of wet granulation) of test compound by oral gavage. Based on the pharmacokinetics of the test compound, dogs are dosed either 1 or 2 hours prior to anesthesia. Dogs are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3-4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40-50 percent inhibition of the hyperemic blood flow response observed after 10-s mechanical occlusion of the LCX. All hemodynamic and ECG measurements are recorded and analyzed with a data acquisition system (Notochord HEM data analysis system, Croissy, France).

Thrombus Formation and Compound Administration Regimens

Electrolytic injury of the intima of the LCX is produced by applying 100-µA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment for a minimum of 30 minutes). The preparation is followed for 4 hours at which time the animal is euthanized and the thrombus is dissected from the LCX and weighed.

Hematology, Coagulation and Template Bleeding Time Determinations

Citrated blood (3 mL, 1 part 3.8% citrate : 9 parts blood) is drawn before drug administration, at 60 min after administration, at 60 min after initiation of vessel injury and just prior to the end of the experiment. Whole blood cell counts, hemoglobin, and hematocrit values are determined on a 40-µL sample of the citrated whole blood with a hematology analyzer (Cell-Dyn 900, Sequoia-Turner, Mount View, Calif., U.S.A.). The remaining blood was cetrifuged at 3,000 g for 5 min to prepare cell-free plasma. Plasma clotting times, prothrombin time (PT) and activated partial thromboplastin times (APTT) were performed using standard Dade reagents and the Coa-Screener coagulation device (American Labor, Largo, Fla.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Dunnet's post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, (1993), 21, 587-599.

Compounds of the instant invention are potent anticoagulant and antithrombotic agents which exhibit particularly good plasma exposure following oral administration, as well as desirable volume of distribution and tissue selectivity properties, as evidenced by standard pharmacokinetic/pharmcodynamic and brain flux assays.

The following Examples are provided to further describe the invention and are not to be construed as limitations thereof.

The abbreviations, symbols and terms used in the examples have the following meanings.

Ac=acetyl
Analysis=elemental analysis
aq=aqueous
Boc=t-butyloxycarbonyl
Calcd=calculated
conc=concentrated
DME=1,2-dimethoxyethane
DMF=dimethylformamide
DMSO=dimethylsulfoxide
EtOAc=ethyl acetate
EtOH=ethanol
MeOH=methanol
HPLC=High Performance Liquid Chromatography
IR=Infrared Spectrum
APCI-MS=atmospheric pressure chemical ionization mass spectrum
ESI-MS (or ES-MS)=electrospray ionization mass spectrum
FD-MS=field desorption mass spectrum
IS-MS=ion spray mass spectrum
GC/MS=gas chromatography mass spectroscopy
NMR=Nuclear Magnetic Resonance RPHPLC=Reversed Phase High Performance Liquid Chromatography
RT (or R$_t$)=retention time
satd=saturated
SCX=strong cation exchange (resin)
TFA=trifluoroacetic acid
THF=tetrahydrofuran Unless otherwise stated, pH adjustments and work up are with aqueous acid or base solutions. $^1$H-NMR indicates a satisfactory proton NMR spectrum was obtained for the compound described. Perdeuterated solvents were used. IR indicates a satisfactory infra red spectrum was obtained for the compound described.

Analytical HPLC method was a linear gradient of 90/10 to 50/50 (0.1% TFA in water/0.1% TFA in acetonitrile) over 40 minutes with a flow rate of 1 mL/min.

Preparation of Nitro-Amide (NA) Intermediates

General Procedure NA-A

2-Nitro-N-(5-methylpyridin-2-yl)benzamide

To a stirring solution of 2-amino-5-methylpyridine (3.1 g, 29 mmol) in dichloromethane (200 mL) was added pyridine (7.3 mL, 90 mmol) followed by 2-nitrobenzoyl chloride (5.7 g, 30 mmol). After 4 h, the solvent was removed in vacuo and the residue was partitioned between ethyl acetate (500 mL) and water (250 mL). The organic phase was separated and washed with water, brine, dried (MgSO$_4$) and filtered, and then concentrated in vacuo to a volume of about 100 mL (precipitate observed). The mixture was then sonicated and allowed to stand overnight then filtered. The collected solid was then washed with diethyl ether, filtered and dried under vacuum to give 3.9 g (52%) of the title compound.

$^1$H-NMR
FD-MS, m/e 256.9 (M+).
Analysis for C$_{13}$H$_{11}$N$_3$O$_3$:
Calc: C, 60.70; H, 4.31; N, 16.33.
Found: C, 61.21; H, 4.32; N, 16.63.

General Procedure NA-B

4-Chloro-N-(5-chloropyridin-2-yl)-2-nitrobenzamide

To a stirring suspension of 4-chloro-2-nitrobenzoic acid (20 g, 99 mmol) in dichloromethane (500 mL) was added a few drops of DMF, followed by oxalyl chloride (15.1 g, 119 mmol). After 1 h, the solvent was removed in vacuo and the residue was dissolved in dichloromethane (500 mL); To this stirring solution was added pyridine (24 mL, 297 mmol) followed by 2-amino-5-chloropyridine (12.7 g, 99 mmol). After stirring overnight, the solvents were removed in vacuo and the residue was stirred vigorously with ethyl acetate and water for several hours. The mixture was filtered to give a white solid, which was washed with ethyl acetate and dried in vacuo to give 23 g (74%) of the title compound. The combined ethyl acetate washings and extract were then washed twice with 1 M citric acid, once with brine, twice with saturated aq sodium bicarbonate, and again with brine. The organic phase was then dried with MgSO$_4$, filtered and concentrated in vacuo. The solid was then suspended in diethyl ether, sonicated and filtered to give a second crop of the title compound as a white solid (5.79 g, 19%).

$^1$H-NMR
IS-MS, m/e 312.0 (M+1)
Analysis for C$_{12}$H$_7$N$_3$O$_3$Cl$_2$:
Calcd: C, 46.18; H, 2.26; N, 13.46.
Found: C, 46.24; H, 2.37; N, 13.43.

Preparation of Intermediates NA-1–NA-12

The following exemplary nitro-amide intermediates were prepared using a conventional procedure such as that of General Procedure NA-A or General Procedure NA-B, or as otherwise described.

Intermediate NA-1

5-Fluoro-2-nitro-N-(5-fluoropyridin-2-yl)benzamide

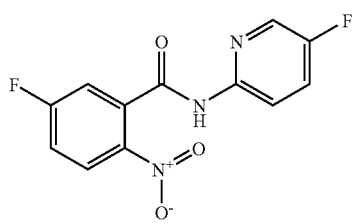

$^1$H-NMR
ESI-MS, m/e 278.09 (M−1).

The starting 5-fluoro-2-nitrobenzoic acid is prepared from 5-fluoro-2-nitrotoluene using a procedure similar to that for the preparation of 4-fluoro-2-nitrobenzoic acid which follows:

To a stirring solution of KMnO$_4$ (76 g, 483 mmol) in water (1 L) was added 4-fluoro-2-nitrotoluene and the solution was heated to reflux. After 4 h, the hot mixture was filtered and the filtrate was cooled with ice, washed with diethyl ether, acidified with conc HCl, and then extracted twice with diethyl ether. The combined ether extracts were washed with brine, dried with MgSO$_4$, filtered and concentrated in vacuo to give 12.07 g (34%) of a white solid.

$^1$H-NMR
IS-MS, m/e 184.0 (M−1).
Analysis for C$_7$H$_4$NO$_4$F:
Calcd: C, 45.42; H, 2.18; N, 7.57.
Found: C, 45.63; H, 2.30; N, 7.61.

Intermediate NA-2

5-Fluoro-2-nitro-N-(5-chloropyridin-2-yl)benzamide

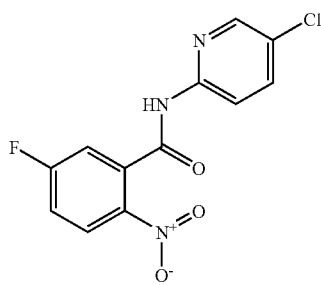

$^1$H-NMR
ESI-MS, m/e 296.22 (M+1).
Analysis for C$_{12}$H$_7$ClFN$_3$O$_3$:
Calcd: C,48.75; H,2.39; N,14.21.
Found: C,48.57; H,2.37; N,14.19.

Intermediate NA-3

5-Chloro-2-nitro-N-(5-fluoropyridin-2-yl)benzamide

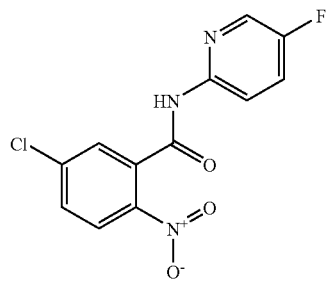

¹H-NMR
ESI-MS, m/e 296.24 (M+1).
Analysis for $C_{12}H_7ClFN_3O_3$:
Calcd: C, 48.75; H, 2.39; N, 14.21.
Found: C, 48.97; H, 2.61; N, 14.13.
¹H-NMR
IS-MS, m/e 184.0 (M−1).
Analysis for $C_7H_4NO_4F$:
Calcd: C, 45.42; H, 2.18; N, 7.57.
Found: C, 45.63; H, 2.30; N, 7.61.

Intermediate NA-4

5-Chloro-2-nitro-N-(5-chloropyridin-2-yl)benzamide

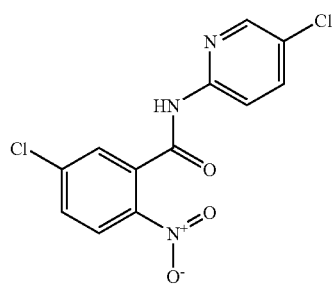

¹H-NMR
ESI-MS, m/e 311.96 (M+1).
Analysis for $C_{12}H_7Cl_2N_3O_3$:
Calcd: C, 46.18; H, 2.26; N, 13.46.
Found: C, 46.24; H, 2.22; N, 13.29.

Intermediate NA-5

5-Chloro-2-nitro-N-(5-methylpyridin-2-yl)benzamide

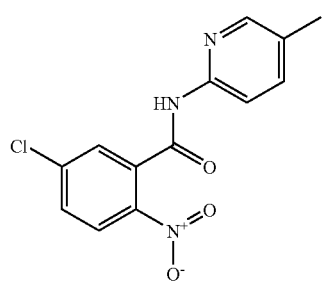

¹H-NMR
ESI-MS, m/e 291.97 (M+1).

Analysis for $C_{13}H_{10}ClN_3O_3$:
Calcd: C, 53.53; H, 3.46; N, 14.41.
Found: C, 53.76; H, 3.41; N, 14.35.

Intermediate NA-6

5-Methyl-2-nitro-N-(5-fluoropyridin-2-yl)benzamide

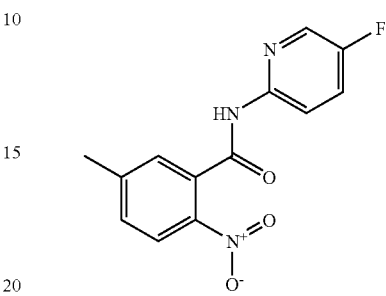

¹H-NMR
APCI-MS, m/e 276 (M+1)

Intermediate NA-7

5-Methyl-2-nitro-N-(5-chloropyridin-2-yl)benzamide

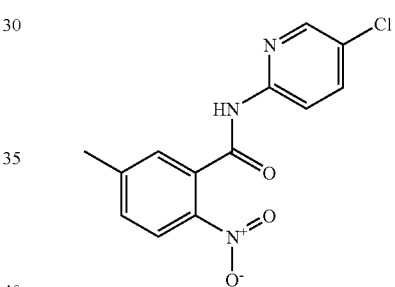

¹H-NMR
ESI-MS, m/e 292 (M+1).
Analysis for $C_{13}H_{10}ClN_3O_3$:
Calcd: C, 53.53; H, 3.46; N, 14.41.
Found: C, 53.52; H, 3.56; N, 14.49.

Intermediate NA-8

5-Methyl-2-nitro-N-(5-methylpyridin-2-yl)benzamide

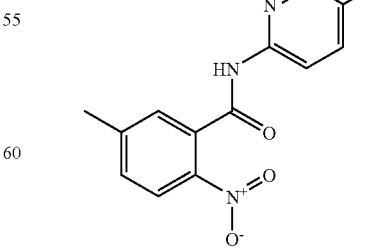

¹H-NMR
ESI-MS, m/e 272.37 (M+1).

Intermediate NA-9

4,5-Difluoro-2-nitro-N-(5-chloropyridin-2-yl)benzamide

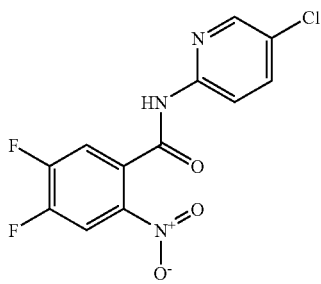

¹H-NMR
ESI-MS, m/e 313.95 (M+1).
Analysis for $C_{12}H_6ClF_2N_3O_3$:
Calcd: C, 45.95; H, 1.93; N, 13.40.
Found: C, 45.77; H, 2.00; N, 13.43.

Intermediate NA-10

Compound AA-10 prepared via 4-amino-3-iodoacetophenone

Intermediate NA-11

4-Methoxycarbonyl-2-nitro-N-(5-chloropyridin-2-yl)benzamide

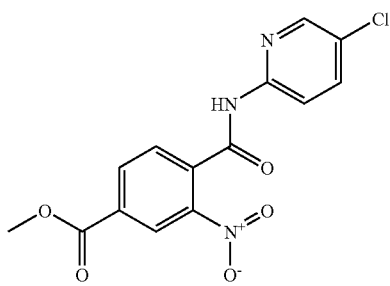

¹H-NMR
ESI-MS, m/e 336.09 (M+1).
Analysis for $C_{14}H_{10}ClN_3O_5$:
Calcd: C, 50.09; H, 3.00; N, 12.52.
Found: C, 49.83; H, 3.08; N, 12.25.

Intermediate NA-12

5-Methoxycarbonyl-2-nitro-N-(5-chloropyridin-2-yl)benzamide

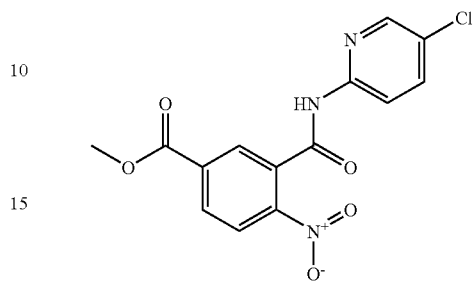

¹H-NMR
ESI-MS, m/e 336.07 (M+1).
Analysis for $C_{14}H_{10}ClN_3O_5$:
Calcd: C, 50.09; H, 3.00; N, 12.52.
Found: C, 50.37; H, 3.08; N, 12.52.

Preparation of Amino-Amide (AA) Intermediates

General Procedure AA-A

N-(5-Methylpyridin-2-yl)-2-aminobenzamide

To a stirring solution of N-(5-methylpyridin-2-yl)-2-nitrobenzamide (1.5 g, 5.8 mmol) and Ni(OAC)₂.4H₂O (2.9 g, 11.7 mmol) in THF (20 mL) and methanol (40 mL) at 0° C. was added, in small portions, sodium borohydride (0.88 g, 23.2 mmol). After complete addition and an additional 5 min, the solvent was evaporated in vacuo and the residue was partitioned between ethyl acetate (200 mL) and 50% conc NH₄OH (200 mL). The organic phase was separated and washed again with 50% conc NH₄OH, followed by brine, then dried with MgSO₄, filtered and concentrated in vacuo to give 1.25 g (95%) of a light yellow solid.
¹H-NMR
FD-MS, m/e 227.1 (M+).

General Procedure AA-B

N-(5-Chloropyridin-2-yl)-2-aminobenzamide

To a solution of N-(5-chloropyridin-2-yl)-2-nitro-benzamide (2 g, 7.2 mmol) in THF (50 mL) and ethyl acetate (50 mL) was added Raney Ni (0.2 g) and the mixture was placed under hydrogen (4.1 bar) in a high pressure apparatus. After shaking overnight, the mixture was filtered and concentrated in vacuo and purified by flash chromatography to give 1.5 g (83%) of an off-white solid.
¹H-NMR

Preparation of Intermediates AA-1-AA-14

The following exemplary amino-amide intermediates were prepared using a conventional procedure such as that of General Procedure AA-A or General Procedure AA-B, or as otherwise described.

Intermediate AA-1

2-Amino-5-fluoro-N-(5-fluoropyridin-2-yl)benzamide

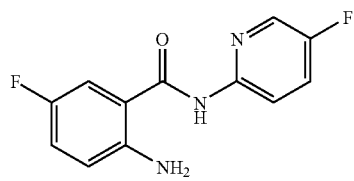

$^1$H-NMR
ESI-MS, m/e 248 (M−1)

Intermediate AA-2

2-Amino-5-fluoro-N-(5-chloropyridin-2-yl)benzamide

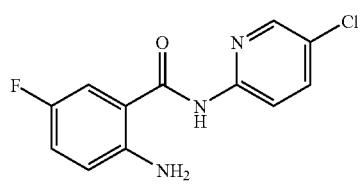

$^1$H-NMR
ESI-MS, m/e 264.17 (M−1).
Analysis for $C_{12}H_9ClFN_3O$:
Calcd: C, 54.25; H, 3.41; N, 15.82.
Found: C, 53.96; H, 3.43; N, 15.54.

Intermediate AA-3

2-Amino-5-chloro-N-(5-fluoropyridin-2-yl)benzamide

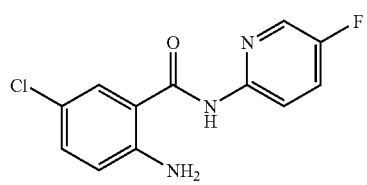

$^1$H-NMR
ESI-MS, m/e 264.13 (M−1).

Intermediate AA-4

2-Amino-5-chloro-N-(5-chloropyridin-2-yl)benzamide

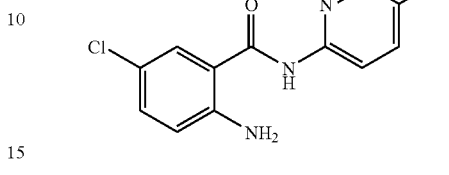

$^1$H-NMR
ESI-MS, m/e 281.12 (M−1).
Analysis for $C_{12}H_9Cl_2N_3O$:
Calcd: C, 51.09; H, 3.22; N, 14.89.
Found: C, 51.19; H, 3.33; N, 14.61.

Intermediate AA-5

2-Amino-5-chloro-N-(5-methylpyridin-2-yl)benzamide

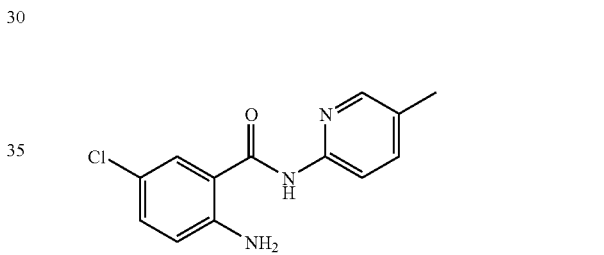

$^1$H-NMR
ESI-MS, m/e 260.02 (M−1).
Analysis for $C_{13}H_{12}ClN_3O$:
Calcd: C, 59.66; H, 4.62; N, 16.06.
Found: C, 59.89; H, 4.57; N, 15.99.

Intermediate AA-6

2-Amino-5-methyl-N-(5-fluoropyridin-2-yl)benzamide

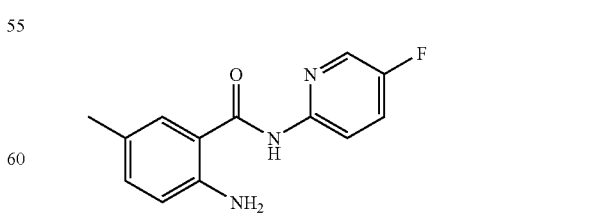
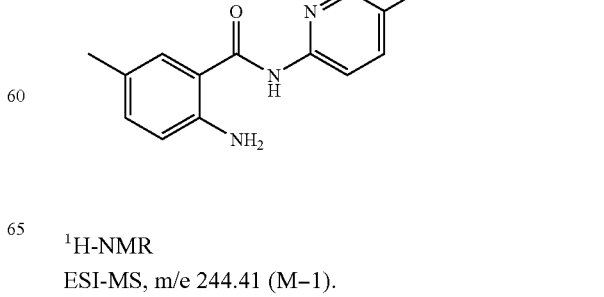

$^1$H-NMR
ESI-MS, m/e 244.41 (M−1).

Intermediate AA-7

2-Amino-5-methyl-N-(5-chloropyridin-2-yl)benzamide

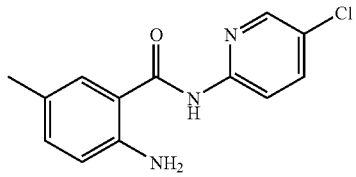

¹H-NMR
ESI-MS, m/e 260.01 (M−1).

Intermediate AA-8

2-Amino-5-methyl-N-(5-methylpyridin-2-yl)benzamide

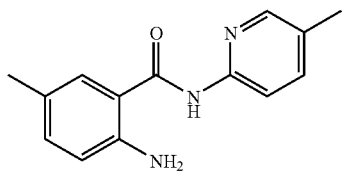

¹H-NMR
ESI-MS, m/e 240.15 (M−1).

Intermediate AA-9

2-Amino-4,5-difluoro-N-(5-chloropyridin-2-yl)benzamide

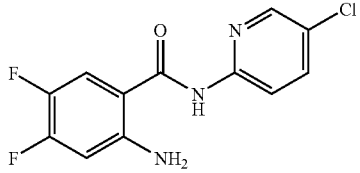

¹H-NMR
ESI-MS, m/e 282.12 (M−1).

Intermediate AA-10

5-Acetyl-2-amino-N-(5-chloropyridin-2-yl)benzamide

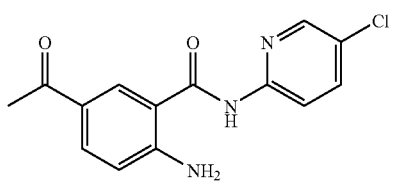

To a stirred solution of 4-aminoacetophenone (50 g, 370 mmol) in ethanol (1 L) and dichloromethane (750 mL) at 0° C. was added iodine (94 g, 370 mmol) and silver sulfate (116 g, 370 mmol). The reaction mixture was stirred at 0° C. for 10 min and then at room temperature for 4 h, filtered and concentrated. The resulting residue was partitioned between dichloromethane and 5 N sodium hydroxide. The organic phase was dried (magnesium sulfate), filtered, and concentrated in vacuo. The crude product was chromatographed over silica gel, eluting with a stepwise gradient from dichloromethane to 10% ethyl acetate in dichloromethane, to give 38.2 g (40%) of 4-amino-3-iodoacetophenone as a yellow oil.

A mixture of 4-amino-3-iodoacetophenone (5.0 g, 19.2 mmol), 2-amino-5-chloropyridine (7.4 g, 54.5 mmol), palladium acetate (431 mg, 1.92 mmol), 1,3-bis(diphenyl-phosphino)propane (2.37 g, 5.75 mmol), triethylamine (5.4 mL, 38.3 mmol) in acetonitrile (100 mL) was shaken under a carbon monoxide atmosphere (54.4 bar) for 16 h. The crude mixture was filtered through diatomaceous earth, and the filtrate was stripped to near dryness and titurated with ethyl ether to remove the excess 2-amino-5-chloropyridine. The product was isolated by SCX column, then flash chromatography using 10% acetonitrile in chloroform. This afforded 1.17 g (21%) of the title product.

¹H-NMR
ESI-MS, m/e 288.1 (M−1).

Intermediate AA-11

2-Amino-4-methoxycarbonyl-N-(5-chloropyridin-2-yl)benzamide

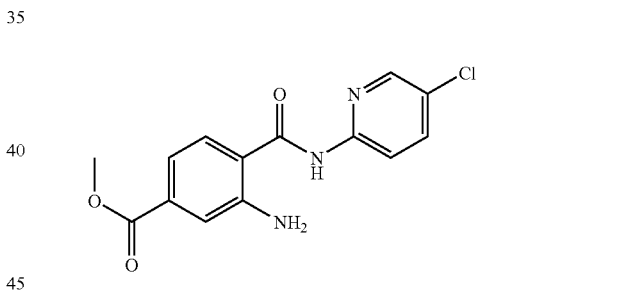

¹H-NMR
ESI-MS, m/e 304.09 (M−1).

Intermediate AA-12

2-Amino-5-methoxycarbonyl-N-(5-chloropyridin-2-yl)benzamide

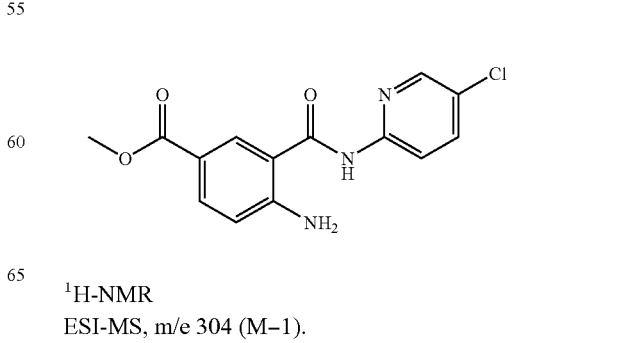

¹H-NMR
ESI-MS, m/e 304 (M−1).

Intermediate AA-13

3-Amino-N-(5-chloropyridin-2-yl)pyridine-2-carboxamide

¹H-NMR

ESI-MS, m/e 247.19 (M−1).

The amine was prepared using a similar procedure to the following:

A (Parr) pressure apparatus was charged with 3-amino-2-chloropyridine (500 mg, 3.89 mmol), 2-amino-5-chloropyridine (1.00 g, 7.78 mmol), palladium acetate (88 mg, 0.39 mmol), 1,3-bis(diphenylphosphino)propane (483 mg, 1.17 mmol) and triethylamine (590 mg, 5.84 mmol). The mixture was placed under a carbon monoxide atmosphere (4.1 bar) and heated at 100° C. After 72 h, the mixture was filtered, concentrated and the residue purified by column chromatography (SiO$_2$:0 to 5% EtOAc in methylene chloride) affording 550 mg (57%) of the title compound.

¹H-NMR, IR

IS-MS, m/e 249 (M+1).

Analysis for $C_{11}H_9ClN_4O$:

Calcd: C, 53.13; H, 3.65; N, 22.53.

Found: C, 53.40; H, 3.66; N, 22.45.

Intermediate AA-14

3-Amino-N-(5-chloropyridin-2-yl)-6-methylpyridine-2-carboxamide

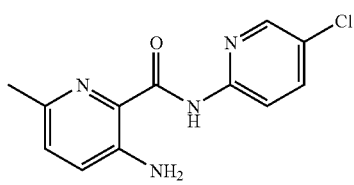

Using methods substantially equivalent to those described above for Intermediate AA-13, 3-amino-N-(5-chloro-pyridin-2-yl)-6-methylpyridine-2-carboxamide (16 g, 46%) was prepared from 3-amino-2-chloro-6-methylpyridine and 2-amino-5-chloropyridine.

¹H NMR

ESI-MS, m/e 263.1 (M+1).

Preparation of Intermediates A-1-A-12

The following intermediates were prepared by acylation of the requisite amine using 5-chloropyrazine-2-carbonyl chloride and a procedure similar to that described for the preparation of Intermediate A-1, or as otherwise described.

Intermediate A-1

2-(5-Chloropyrazin-2-ylcarbonylamino)-5-fluoro-N-(5-chloro-pyridin-2-yl)benzamide

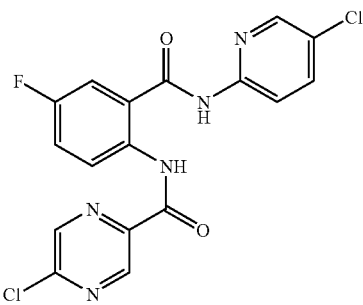

To a stirred mixture of thionyl chloride (75 mL), toluene (25 mL) and DMF (0.2 niL) was added 5-hydroxy-pyrazine-2-carboxylic acid (8 g, 57 mmol). The mixture was heated at 80° C. for 3.5 h. Evaporation of the solvent under vacuum provided the solid acid chloride which was dissolved in methylene chloride (100 mL).

To a cooled (0° C.) suspension of 2-amino-5-fluoro-N-(5-chloropyridin-2-yl)benzamide (13.815 g, 52 mmol) in methylene chloride (200 mL) and pyridine (5.86 g, 6 mL, 74 mmol) was added dropwise the solution of acid chloride from step 1 above over a period of 15-30 min. The reaction mixture was stirred at room temperature overnight. Water (100 mL) was added, and the mixture stirred 30 min before the solids were filtered. The solids were washed with water (100 mL) and dried under vacuum. The solids were slurried in ether (100 mL), sonicated for 15 min, filtered and dried.

Yield=19.6 g.

¹H-NMR (DMSO) δ 9.13 (d, J=1.1 Hz), 8.97 (d, J=1.1 Hz), 8.55 (dd, J=9.1 Hz, and 5.1 Hz), 8.47 (d, J=2.6 Hz), 8.11 (d, J=8.8 Hz), 8.01 (dd, J=9.1 Hz, and 2.6 Hz), 7.82 (dd, J=9.5 Hz, and 2.9 Hz) 7.5-7.6 (m).

ESI-MS, m/e 406.3 (M+1).

Intermediate A-2

5-Chloro-2-(5-chloropyrazin-2-ylcarbonylamino)-N-(5-fluoro-pyridin-2-yl)benzamide

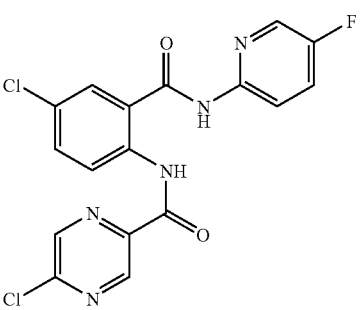

¹H-NMR

ESI-MS, m/e 404.1 (M−1).

Intermediate A-3

5-Chloro-2-[5-chloropyrazin-2-ylcarbonylamino]-N-(5-chloro-pyridin-2-yl)benzamide

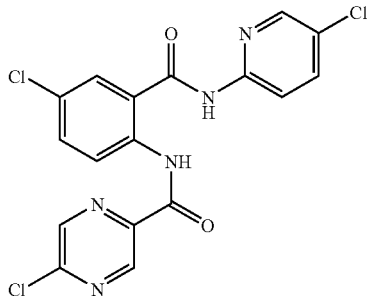

$^1$H-NMR (CDCl$_3$) δ 9.25 (d, J=1.1 Hz), 8.83 (d, J=9.1 Hz), 8.71 (d, J=1.1 Hz), 8.62 (br, s), 8.23-8.30 (m), 7.8-7.72 (m), 7.59 (dd, J=8.8 Hz and 2.6 Hz).
FIA-MS, m/e 423.49 (M+1).
Analysis for C$_{17}$H$_{10}$Cl$_3$N$_5$O$_2$:
Calcd: C, 48.31; H, 2.38; N, 16.57.
Found: C, 47.87; H, 2.31; N, 16.39.

Intermediate A-4

5-Chloro-2-[5-chloropyrazin-2-ylcarbonylamino]-N-(5-methyl-pyridin-2-yl)benzamide

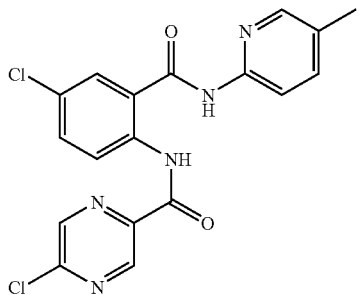

$^1$H-NMR (DMSO) δ 9.13 (d, J=1.1 Hz), 8.98 (d, J=1.1 Hz), 8.62 (d, J=8.8 Hz), 8.25 (br, s), 8.03 (d, J=2.6 Hz), 7.96 (d, J=8.4 Hz), 7.71 (dd, J=10.5 Hz and 2.2 Hz), 2.30 (s).
ESI-MS, m/e 402.17 (M+1).

Intermediate A-5

2-[5-Chloropyrazin-2-ylcarbonylamino]-5-methyl-N-(5-fluoro-pyridin-2-yl)benzamide

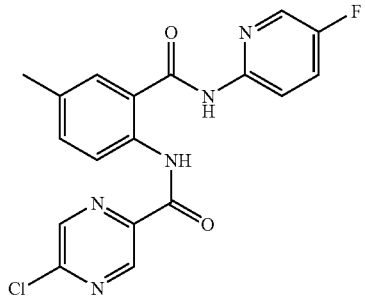

$^1$H-NMR
ESI-MS, m/e 384.1 (M−1).

Intermediate A-6

2-(5-Chloropyrazin-2-ylcarbonylamino)-5-methyl-N-(5-chloro-pyridin-2-yl)benzamide

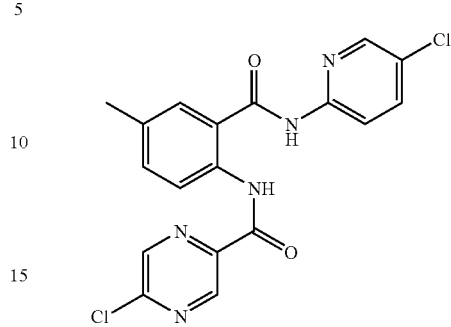

$^1$H-NMR (DMSO) δ 9.12 (d, J=1.5 Hz), 8.97 (d, J=1.5 Hz), 8.29-8.46 (m), 8.12 (d, J=8.4 Hz), 8.00 (dd, J=9.1 Hz and 2.6 Hz), 7.82 (d, J=1.5 Hz), 7.46 (dd, J=8.4 Hz and 1.8 Hz), 2.36 (s)
ESI-MS, m/e 402.2 (M+1).

Intermediate A-7

2-(5-Chloropyrazin-2-ylcarbonylamino)-5-methyl-N-(5-methyl-pyridin-2-yl)benzamide

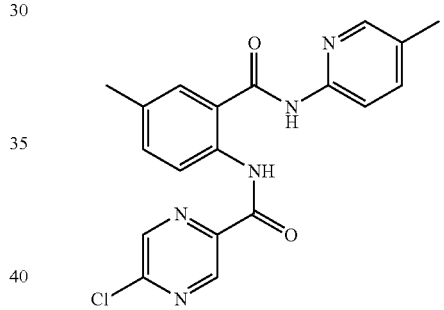

$^1$H-NMR (DMSO) δ 9.14 (d, J=1.5 Hz), 8.99 (d, J=1.2), 8.51 (d, J=8.5 Hz), 8.25 (d, br, J=1.5), 8.00 (d, J=8.2 Hz), 7.84 (d, J=1.5 Hz), 7.71 (dd, J=9.4 Hz and 2.1 Hz), 7.46 (dd, J=10 Hz and 1.4 Hz), 2.37 (s), 2.31 (s).
ESI-MS, m/e 380.33 (M−1).

Intermediate A-8

2-(5-Chloropyrazin-2-ylcarbonylamino)-4,5-difluoro-N-(5-chloropyridin-2-yl)benzamide

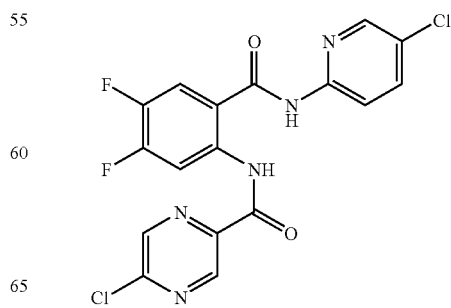

¹H-NMR (DMSO) δ 9.14 (d, J=1.5 Hz), 8.98 (d, J=1.1 Hz), 8.59-8.66 (m), 8.48 (d, J=2.6 Hz), 8.08-8.19 (m), 8.01 (dd, J=9.0 Hz and 2.4 Hz).
ESI-MS, m/e 424.04 (M+1).
Analysis for $C_{17}H_9Cl_2F_2N_5O_2$:
Calcd: C, 48.14; H, 2.14; N, 16.51.
Found: C, 47.65; H, 2.26; N, 16.04.

Intermediate A-9

5-Acetyl-2-(5-chloropyrazin-2-ylcarbonylamino)-N-(5-methyl-pyridin-2-yl)benzamide

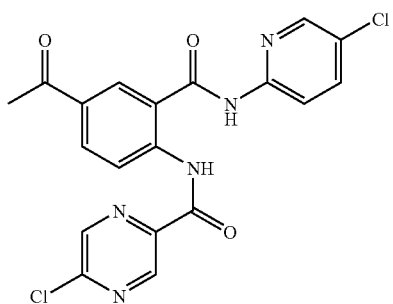

¹H-NMR (DMSO) δ 9.16 (d, J=1.3 Hz), 9.00 (d, J=1.3 Hz), 8.76 (d, J=8.8 Hz), 8.54 (d, J=2.0 Hz), 8.50 (d, J=2.0 Hz), 8.12 8.23 (m), 8.03 (dd, J=8.9 Hz and 2.6 Hz), 2.66 (s).
ESI-MS, m/e 430.18 (M+1).
Analysis for $C_{19}H_{13}Cl_2N_5O_3$:
Calcd: C, 53.04; H, 3.04; N, 16.28.
Found: C, 53.07; H, 3.07; N, 15.96.

Intermediate A-10

2-(5-Chloropyrazin-2-ylcarbonylamino)-4-methoxycarbonyl-N-(5-chloropyridin-2-yl)benzamide

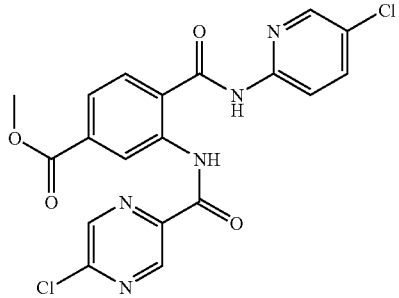

¹H-NMR (DMSO) δ 9.16 (dd, J=3.7 Hz and 1.5 Hz), 8.98 (d, J=1.5 Hz), 8.48 (d, J=2.2 Hz), 8.01-8.15 (m), 7.82 (dd, J=8.1 Hz and 1.6 Hz), 3.39 (s).
ESI-MS, m/e 446.08 (M+1).
Analysis for $C_{19}H_{13}Cl_2N_5O_4$:
Calcd: C, 51.14; H, 2.94; N, 15.69.
Found: C, 50.83; H, 2.89; N, 15.17.

Intermediate A-11

2-(5-Chloropyrazin-2-ylcarbonylamino)-5-methoxycarbonyl-N-(5-chloropyridin-2-yl)benzamide

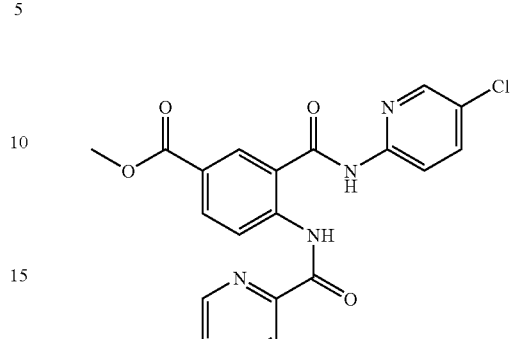

¹H-NMR (DMSO) δ 9.16 (d, J=1.5 Hz), 9.00 (d, J=1.1 Hz), 8.74 (d, J=8.8 Hz), 8.50 (dd, J=6.8 Hz and 2.4 Hz), 8.21 (dd, J=8.8 Hz and 1.8 Hz), 8.13 (d, J=8.8 Hz), 8.02 (dd, J=8.8 Hz and 2.6 Hz), 3.90 (s).
FD-MS, m/e 445.62 (M−1).
Analysis for $C_{19}H_{13}Cl_2N_5O_4$
Calcd: C, 51.14; H, 2.94; N, 15.69.
Found: C, 50.84; H, 2.80; N, 15.40.

Intermediate A-12

3-(5-Chloropyrazin-2-ylcarbonylamino)-N-(5-chloropyridin-2-yl)pyridine-2-carboxamide

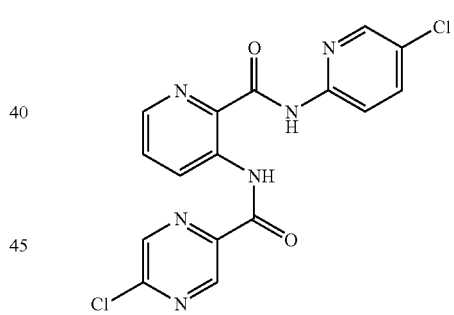

¹H-NMR (DMSO) δ 9.28 (dd, J=8.4 Hz and 1.0 Hz), 9.19 (d, J=1.1 Hz), 9.07 (d, J=1.1 Hz), 8.48-8.54 (m), 8.26 (d, J=8.8 Hz), 8.10 (dd, J=8.8 Hz and 2.6 Hz), 7.81-7.86 (m).
ESI-MS, m/e 389.10 (M+1).

Preparation of Intermediates B-1-B-8

The following intermediates were prepared by acylation of the requisite amine using 6-chloropyridazine-3-carbonyl chloride and a procedure similar to that described for the preparation of Intermediate A-1, or as otherwise described.
The 6-chloropyridazine-3-carbonyl chloride is conveniently prepared by conventional procedures as follows (Reference: J. Chem. Soc. 1948 2195-2198).
To a stirred solution of 3-chloro-6-methylpyridazine (11 g, 86 mmol) in $H_2SO_4$ (100 mL) at 45° C. was added portionwise $K_2Cr_2O_7$ (30.3 g). The reaction was stirred at 45° C. for 4 h. The mixture was poured over ice and the resulting aqueous solution extracted with ethyl ether until no further product was obtained (about 4 L). The extracts were dried (Na$_2$SO$_4$), filtered and the solvent removed. The resulting residue was dissolved in CH$_2$Cl$_2$ (20 mL) and triturated with hexanes. This afforded 5.1 g (32.2 mmol, 37% yield) of 6-chloropyridazine-3-carboxylic acid as a white solid.

To a solution of the acid (951 mg, 6.0 mmol) in CH$_2$Cl$_2$ (100 mL) at 0° C. was added pyridine (0.64 mL, 7.9 mmol) and DMF (2 drops) followed by oxalyl chloride (3.3 mL of a 2 M solution in CH$_2$Cl$_2$, 6.6 mmol). This was stirred at 0° C. for 30 min, then at room temperature for 1 h. This material was used without purification.

Intermediate B-1

2-(6-Chloropyridazin-3-ylcarbonylamino)-5-fluoro-N-(5-chloropyridin-2-yl)benzamide

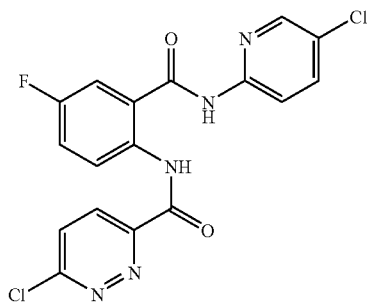

$^1$H-NMR (CDCl$_3$) δ 8.83-8.87 (m), 8.64 (s, br), 8.44 (d, J=9.1 Hz), 8.34 (d, J=8.8 Hz), 8.27 (s, br), 7.72-7.79 (m), 7.48 (dd, J=8.7 Hz and 2.7 Hz), 7.32-7.38 (m).

ESI-MS, m/e 406.35 (M+1).

Intermediate B-2

5-Chloro-2-(6-chloropyridazin-3-ylcarbonylamino)-N-(5-chloropyridin-2-yl)benzamide

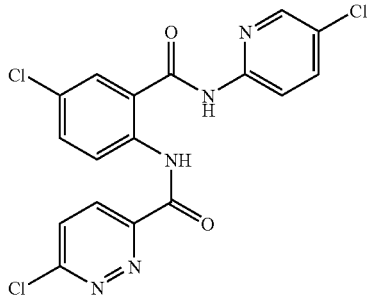

$^1$H-NMR (CDCl$_3$) δ 8.84 (d, J=8.8 Hz), 8.62 (s, br), 8.43 (d, J=8.8 Hz), 8.34 (d, J=8.8 Hz), 8.28 (s, br), 7.78 (d, J=2.2 Hz), 7.72-7.75 (m), 7.57-7.61 (2d, J$_1$=2.2 Hz, J$_2$=2.6 Hz).

ESI-MS, m/e 421.94 (M+1).

Intermediate B-3

5-Chloro-2-(6-chloropyridazin-3-ylcarbonylamino)-N-(5-methylpyridin-2-yl)benzamide

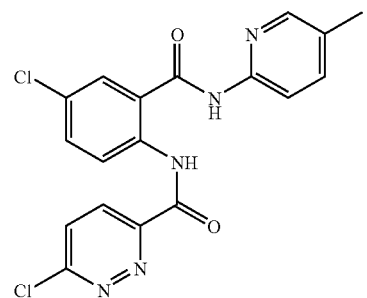

$^1$H-NMR (CDCl$_3$) δ 8.61 (d, J=9.1 Hz), 8.36 (d, J=8.8 Hz), 8.24 (s, br), 8.17 (d, J=8.8 Hz), 8.00-8.05 (m), 7.71 (dd, J=9.0 Hz and 2.4 Hz), 2.30 (s).

ESI-MS, m/e 402.17 (M+1).

Analysis for C$_{18}$H$_{13}$Cl$_{12}$N$_5$O$_2$

Calcd: C, 53.75; H, 3.26; N, 17.41.

Found: C, 53.66; H, 3.30; N, 17.18.

Intermediate B-4

2-(6-Chloropyridazin-3-ylcarbonylamino)-5-methyl-N-(5-chloropyridin-2-yl)benzamide

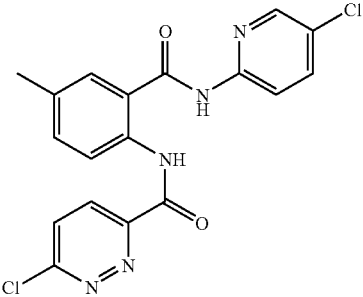

$^1$H-NMR (DMSO) δ 8.46-8.49 (m), 8.35 (d, J=8.8 Hz), 8.15-8.21 (m), 8.00 (d, J=8.8 Hz and 2.6 Hz), 7.84 (d, J=1.5 Hz), 7.47 (d, J=8.4 Hz), 2.37 (s).

ESI-MS, m/e 402.13 (M+1).

Intermediate B-5

2-(6-Chloropyridazin-3-ylcarbonylamino)-5-methyl-N-(5-methylpyridin-2-yl)benzamide

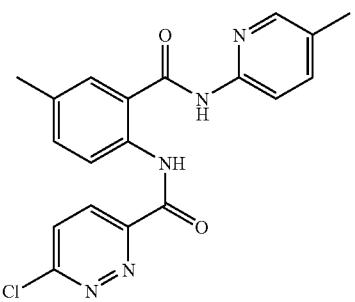

$^1$H-NMR (DMSO) δ 8.50 (d, J=8.4 Hz), 8.35 (d, J=8.8 Hz), 8.23 (s, br), 8.16 (d, J=8.8 Hz), 8.04 (d, J=8.4 Hz), 7.85 (s), 7.70 (dd, J=8.4 Hz and 1.8 Hz), 7.45 (d, J=8.4 Hz), 2.37 (s), 2.29 (s).
ESI-MS, m/e 382.24 (M+1).
Analysis for $C_{19}H_{16}ClN_5O_2$:
Calcd: C, 59.77; H, 4.22; N, 18.34.
Found: C, 59.72; H, 4.26; N, 18.13.

Intermediate B-6

5-Acetyl-2-(3-Chloropyridazin-6-ylcarbonylamino)-N-(5-chloropyridin-2-yl)benzamide

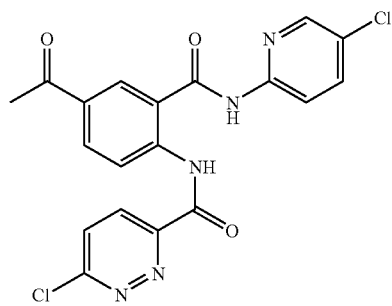

$^1$H-NMR
ESI-MS, m/e 430.09 (M+1).

Intermediate B-7

2-(6-Chloropyridazin-3-ylcarbonylamino)-4-methoxycarbonyl-N-(5-chloropyridin-2-yl)benzamide

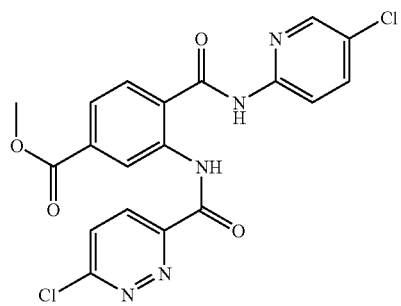

$^1$H-NMR (DMSO) δ 9.16 (d, J=1.5 Hz), 8.48 (d, J=2.6 Hz), 8.38 (d, J=8.8 Hz), 8.19 (d, J=8.8 Hz), 8.00-8.10 (m), 7.84 (dd, J=8.4 Hz and 1.5 Hz), 3.93 (s).
ESI-MS, m/e 446.08 (M+1).

Intermediate B-8

3-(6-Chloropyridazin-3-ylcarbonylamino)-N-(5-chloropyridin-2-yl)pyridine-2-carboxamide

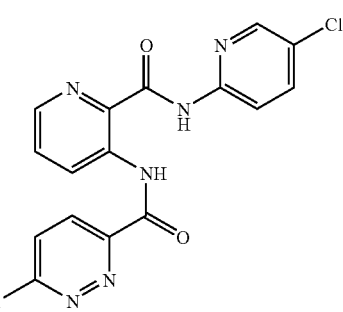

$^1$H-NMR (CDCl$_3$) δ 9.36 (dd, J=8.8 Hz and 1.5 Hz), 8.53 (d, J=8.8 Hz), 8.32-8.41 (m), 7.72-7.77 (m), 7.57-7.61 (m).
ESI-MS, m/e 388.61 (M+1).

Preparation of Intermediates C-1-C-3

The following intermediates were prepared by acylation of the requisite amine using 5-fluoropyrimidine-2-carbonyl chloride and a procedure similar to that described for the preparation of Intermediate A-1, or as otherwise described.

The 5-fluoropyrimidine-2-carbonyl chloride is conveniently prepared by conventional procedures as follows (Reference: Organic Preparations and Procedures Int., Vol. 27, No. 5, 1995, 600-602).

In a 2 L three neck flask equipped with a reflux condenser and an overhead stirrer was placed THF (500 mL), 2,4-dichloro-5-fluoropyrimidine (20 g, 120 mmol) and zinc (23.5 g, 360 mmol). This mixture was stirred vigorously and heated to reflux. To this was added over a 1 h period acetic acid. The reaction was stirred at reflux and monitored by GC/MS until complete. The reaction mixture was allowed to cool to room temperature, then poured into a solution of ethylenediaminetetraacetic acid tetrasodium salt in H$_2$O. This was stirred at room temperature overnight. Diatomaceous earth was added, and the mixture filtered with ether washing. The ether solution was washed with brine, dried (Na$_2$SO$_4$), filtered, and the solvent removed, affording 5.1 g (38.5 mmol, 32% yield) of 2-chloro-5-fluoropyrimidine.

Using procedures similar to those described below for the preparation of 5-fluoropyridine-2-carbonyl chloride from 2-bromo-5-fluoropyridine, 2-chloro-5-fluoropyrimidine was converted into 5-fluoropyrimidine-2-carbonyl chloride.

Intermediate C-1

5-Fluoro-2-(5-fluoropyrimidin-2-ylcarbonylamino)-
N-(5-fluoropyridin-2-yl)benzamide

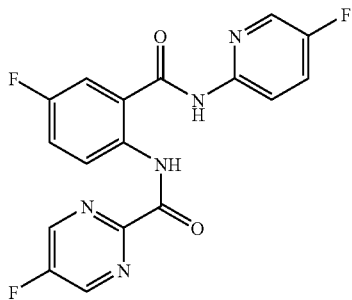

$^1$H-NMR
ESI-MS, m/e 372.07 (M−1).

Intermediate C-2

5-Fluoro-2-(5-fluoropyrimidin-2-ylcarbonylamino)-
N-(5-chloropyridin-2-yl)benzamide

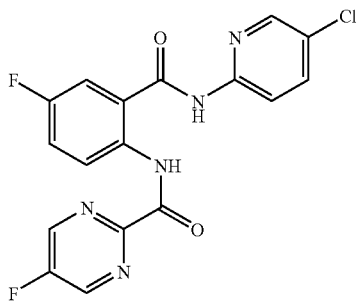

$^1$H-NMR
ESI-MS, m/e 388 (M−1)
Analysis for $C_{17}H_{10}ClF_2N_5O_2$:
Calcd: C, 52.39; H, 2.59; N, 17.97.
Found: C, 52.44; H, 2.44; N, 17.77.

Intermediate C-3

2-(5-Fluoropyrimidin-2-ylcarbonylamino)-5-chloro-
N-(5-chloropyridin-2-yl)benzamide

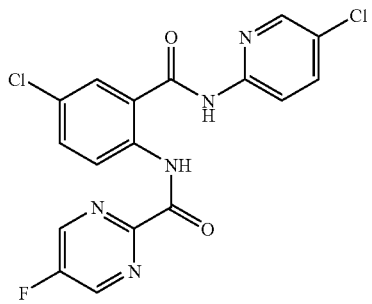

$^1$H-NMR
ESI-MS, m/e 403.9 (M−1).
Analysis for $C_{19}H_{12}Cl_2FN_3O_2$:
Calcd: C, 50.27; H, 2.48; N, 17.24.
Found: C, 50.32; H, 2.22; N, 16.79.

Preparation of Intermediates D-1-D-6

The following intermediates were prepared by acylation of the requisite amine using 5-fluoropyridine-2-carbonyl chloride and a procedure similar to that described for the preparation of Intermediate A-1, or as otherwise described.

The 5-fluoropyridine-2-carbonyl chloride conveniently is prepared by conventional procedures as follows (Reference: Org. Syn. Collective Vol. 3, 136).

To HBr (222 mL, 48%, 1.96 M) at 0° C. was added portion-wise over 10 min 2-amino-5-fluoropyridine (50 g, 446 mmol) followed by drop-wise addition of Br$_2$ (67 mL, 1.32 mol) over 20 min. A solution of NaNO$_2$ (77.5 g, 1.12 mol) in H$_2$O (150 mL) was added drop-wise over 1 h, maintaining the temperature at 0° C. This was stirred at 0° C. for 30 min, and a solution of NaOH (168 g, 4.2 mol) in H$_2$O (168 mL) was added drop-wise maintaining the tempreature below 10° C. The reaction was then allowed to warm to room temperature and stirred for 20 min. The mixture was extracted with ether (6×500 mL). The extracts were dried (Na$_2$SO$_4$), filtered and the solvent removed. Flash chromatography with 3-10% ethyl acetate in hexanes afforded 72.5 g, 412 mmoles, (92% yield) of 2-bromo-5-fluoropyridine as a deep red oil.

A mixture of 2-bromo-5-fluoropyridine (72.5 g, 412 mmol), palladium(II) acetate (2.5 g, 11.2 mmol), 1,1'-bis(diphenylphosphino)ferrocene (11.9 g, 21.5 mmol), triethylamine (100 mL), CH$_3$OH (350 mL), and DMF (350 mL) were shaken in a pressure apparatus at 80° C. under 4.1 bar (60 psig) carbon monoxide overnight. The crude mixture was diluted with ether (3 L) and filtered through diatomaceous earth. The filtrate was washed with brine (3×500 mL), dried (Na$_2$SO$_4$), filtered and the solvent removed. Flash chromatography, using 10-25% ethyl acetate in hexanes, afforded 26.2 g (169 mmol, 41% yield) of methyl 5-fluoropyridine-2-carboxylate.

To a solution of the ester (5.7 g, 36.8 mmol) in CH$_3$OH (100 mL) at room temperature was added a 1 M solution of lithium hydroxide in H$_2$O (40.4 mL). This was stirred at room temperature overnight. The mixture was diluted with saturated NaHCO$_3$ (200 mL) and washed with ether. The aqueous solution was made acidic with 6 N HCl and extracted with ethyl acetate (5×200 mL). The extracts were washed with brine, dried (MgSO4), filtered and the solvent removed affording 4.73 g (33.5 mmol, 91% yield) of 5-fluoropyridine-2-carboxylic acid.

The 5-fluoropyridine-2-carboxylic acid was converted into 5-fluoropyridine-2-carbonyl chloride using a procedure similar to that described above for the preparation of 6-chloropyridazine-3-carbonyl chloride.

Intermediate D-1

5-Fluoro-2-(5-fluoropyridin-2-ylcarbonylamino)-N-(5-fluoropyridin-2-yl)benzamide

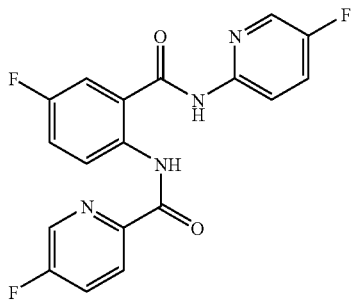

¹H-NMR
ESI-MS, m/e 373.09 (M+1).

Intermediate D-2

5-Fluoro-2-(5-fluoropyridin-2-ylcarbonylamino)-N-(5-chloro-pyridin-2-yl)benzamide

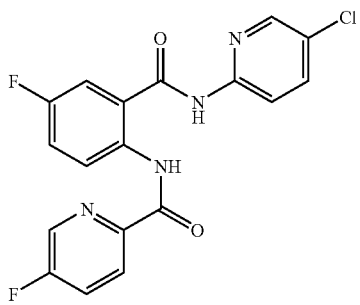

¹H-NMR (DMSO, 250 MHz) δ 8.76 (d, J=2.7 Hz), 8.56-8.62 (m), 8.49 (d, J=2.7 Hz), 8.24-8.29 (m), 8.16 (d, J=8.8 Hz), 7.95-8.05 (m), 7.80 (dd, J=9.2 Hz and 3.1 Hz), 7.49-7.57 (m).
ESI-MS, m/e 389.15 (M+1).

Intermediate D-3

5-Chloro-2-(5-fluoropyridin-2-ylcarbonylamino)-N-(5-chloro-pyridin-2-yl)benzamide

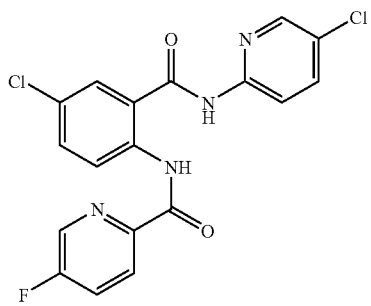

¹H-NMR (DMSO, 250 MHz) δ 7.77 (d, J=3.1 Hz), 8.62 (d, J=9.2 Hz), 8.49 (d, J=2.7 Hz), 8.24-8.29 (m), 8.15 (d, J=8.4 Hz), 7.95-8.05 (m), 7.71 (dd, J=8.8 Hz and 2.4 Hz).
FD-MS, m/e 405.5 (M+1).

Intermediate D-4

5-Chloro-2-(5-fluoropyridin-2-ylcarbonylamino)-N-(5-methyl-pyridin-2-yl)benzamide

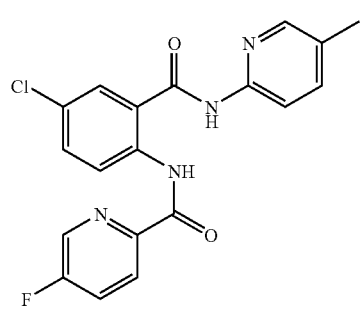

¹H-NMR (DMSO, 250 MHz) δ 8.82 (d, J=2.7 Hz), 8.71 (d, J=8.8 Hz), 8.29-8.34 (m), 8.01-8.08 (m), 7.73-7.80 (m), 2.36 (s).
ESI-MS, m/e 385.08 (M+1).

Intermediate D-5

2-(5-Fluoropyridin-2-ylcarbonylamino)-5-methyl-N-(5-chloro-pyridin-2-yl)benzamide NH

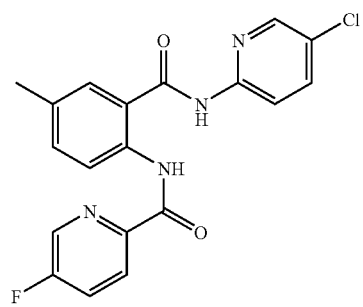

¹H-NMR (DMSO, 250 MHz) δ 8.76 (d, J=3.0), 8.53 (s), 8.47-8.49 (m), 8.23-8.28 (m), 8.16 (d, J=8.8 Hz), 7.94-8.08 (m), 7.79 (d, J=1.5 Hz), 7.46 (dd), 2.37 (s).
ESI-MS, m/e 385.08 (M+1).
Analysis for $C_{19}H_{14}ClFN_4O_2$:
Calcd: C, 59.31; H, 3.67; N, 14.56.
Found: C, 59.17; H, 3.42; N, 14.48.

Intermediate D-6

2-(5-Fluoropyridin-2-ylcarbonylamino)-5-methyl-N-(5-methyl-pyridin-2-yl)benzamide

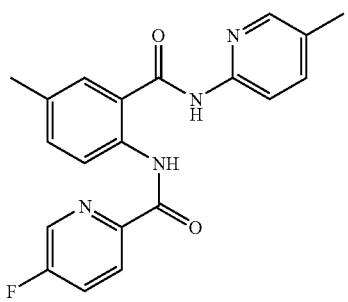

¹H-NMR
ESI-MS, m/e 365.2 (M+1).

Preparation of Intermediates E-1-E-5

The following intermediates were prepared by acylation of the requisite amine using 6-chloropyridine-3-carbonyl chloride and a procedure similar to that described for the preparation of Intermediate A-1, or as otherwise described.

Intermediate E-1

2-(6-Chloropyridin-3-ylcarbonylamino)-5-fluoro-N-(5-chloro-pyridin-2-yl)benzamide

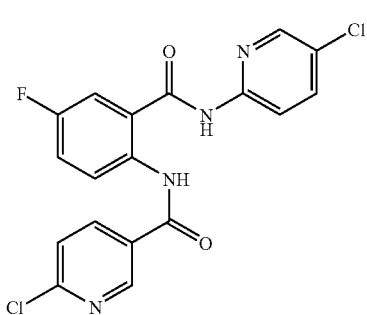

¹H-NMR (DMSO, 250 MHz) δ 8.89 (d, J=2.4 Hz), 8.43 (d, J=2.7 Hz), 8.25-8.30 (m), 8.14 (d, J=8.8 Hz), 7.92-7.98 (m), 7.64-7.74 (m), 7.45-7.53 (m)
ESI-MS, m/e 405.24 (M+1).

Intermediate E-2

5-Chloro-2-(6-chloropyridin-3-ylcarbonylamino)-N-(5-chloro-pyridin-2-yl)benzamide

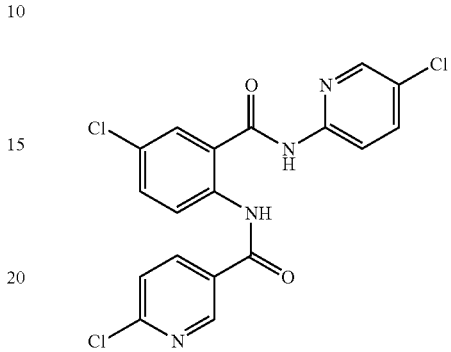

¹H-NMR (DMSO, 250 MHz) δ 8.89 (d, J=2.1), 8.44 (d, J=2.1 Hz), 8.28 (dd, J=8.2 Hz and 2.4 Hz), 8.14 (d, J=9.1 Hz), 7.94-8.03 (m), 7.88 (d, J=2.4), 7.76-7.75 (m).
ESI-MS, m/e 420.93 (M+1).

Intermediate E-3

5-Chloro-2-(⁶-chloropyridin-3-ylcarbonylamino)-N-(5-methyl-pyridin-2-yl)benzamide

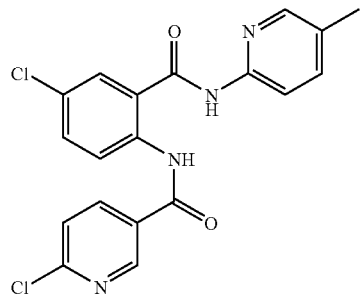

¹H-NMR (DMSO) δ 8.88 (d, J=2.6 Hz), 8.12-8.29 (m), 7.92-7.99 (m), 7.64-7.73 (m), 2.27 (s).
ESI-MS, m/e 401.07 (M+1).

Intermediate E-4

2-(6-Chloropyridin-3-ylcarbonylamino)-4-methoxy-carbonyl-N-(5-chloropyridin-2-yl)benzamide

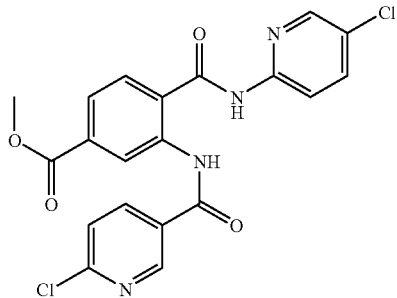

$^1$H-NMR
ESI-MS, m/e 443.17 (M−1).

Intermediate B-5

3-[6-Chloropyridin-3-ylcarbonylamino]-N-(5-chloropyridin-2-yl)pyridine-2-carboxamide

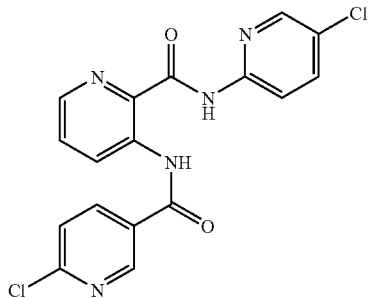

$^1$H-NMR (DMSO) δ 9.08 (d, J=8.4 Hz), 9.00 (s, br), 8.49 - 8.54 (m), 8.37 (d, J=8.4 Hz), 8.28 (d, J=8.4 Hz), 8.06 (d, J=8.8 Hz), 7.83 (d, J=8.1 Hz).
ESI-MS, m/e 386.13 (M−1).

EXAMPLE 1

Preparation of 5-Chloro-2-(6-phenylpyridin-3-ylcarbonyl-amino)-N-(5-chloropyridin-2-yl)benzamide

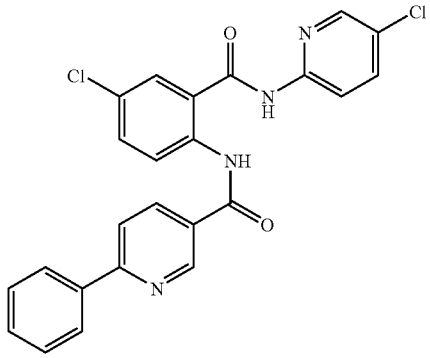

To a solution of 5-chloro-2-(6-chloropyridin-3-yl-carbonylamino)-N-(5-chloropyridin-2-yl)benzamide (Intermediate E-2, 0.42167 g, 1 mmol) in 10 mL of DME was added phenyl boronic acid (0.134 g, 1.1 mmol) and an aqueous solution of potassium phosphate (0.6 mL, 1 molar solution). The reaction mixture was degassed and tetrakistriphenylphosphine palladium (60 mg) was added. The mixture was heated at 80° C. overnight, cooled to room temperature, diluted with ethyl acetate (50 mL), washed with water, saturated sodium bicarbonate, and dried over anhydrous magnesium sulfate. After evaporation of the solvent, the crude product was purified by RPHPLC [ethyl acetate/hexane (3:7)]. Yield=0.280 g.

$^1$H-NMR (DMSO-$d_6$) δ 9.14 (d, J=1.9 Hz), 8.44 (d, J=2.6 Hz), 8.32 (dd, J=8.3 Hz and 2.3 Hz), 7.98 (d, J=2.6 Hz), 7.95 (d, J=2.6 Hz), 7.93 (d, J=2.6 Hz), 7.68 (dd, J=8.7 Hz and 2.6 Hz), 7.50-7.54 (m).
ESI-MS, m/e 463.23 (M+1)
Analysis for $C_{24}H_{16}Cl_2N_4O_2$:
Calcd: C, 62.22; H, 3.48; N, 12.09.
Found: C, 62.01; H, 3.58; N, 12.12.

EXAMPLE 2

Preparation of 5-Chloro-2-[6-(morpholin-4-yl)pyridin-3-yl-carbonylamino]-N-(5-chloropyridin-2-yl)benzamide

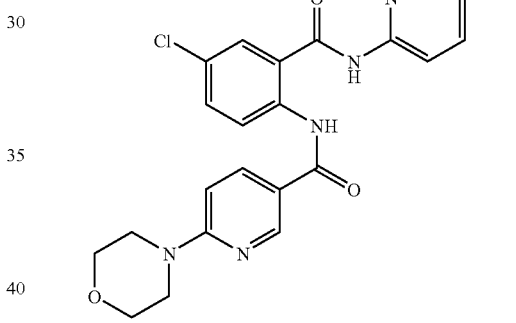

A solution of 5-chloro-2-(6-chloropyridin-3-ylcarbonylamino)-N-(5-chloropyridin-2-yl)benzamide (0.2 g) and morpholine (2 mL) in DMSO (2 mL) was heated at 80° C. in a sealed tube overnight. The mixture was cooled to room temperature, diluted with ethyl acetate (50 mL), washed with water, sodium bicarbonate, and dried over sodium sulfate. After evaporation of the solvent, the product was purified by RPHPLC [ethyl acetate/hexane (3:7)]. Yield=0.054 g.

$^1$H-NMR (CDCl$_3$) δ 8.82-8.88 (m), 8.59 (s, br), 8.30-8.33 (m), 8.11 (dd, J=9.0 and 2.6 Hz), 7.76 (dd, J=9.0 Hz and 2.3 Hz), 7.68 (d, J=2.3 Hz), 7.54 (dd, J=9.0 Hz and 2.6 Hz), 6.69 (d, J=9.0 Hz), 3.82-3.85 (t, J=5.3 Hz and 4.5 Hz), 3.66-3.70 (t, J=5.3 Hz and 4.1 Hz).
ESI-MS, m/e 472.21 (M+1)
Analysis for $C_{22}H_{19}Cl_2N_5O_3$:
Calcd: C, 55.94; H, 4.05; N, 14.83.
Found: C, 55.73; H, 4.10; N, 14.17.

Preparation of Examples 3-22

Unless otherwise indicated, the following examples were prepared from the requisite intermediate described above by using a procedure similar to that of Example 2 and the requisite amine. Where indicated, the requisite t-butoxycarbonyl (Boc) protected diamine was used to provide the indicated protected compound which was deprotected using a procedure similar to that described in Example 8-B.

EXAMPLE 3

5-Chloro-2-[6-(pyrrolidin-1-yl)pyridin-3-ylcarbonylamino]-N-(5-chloropyridin-2-yl)benzamide

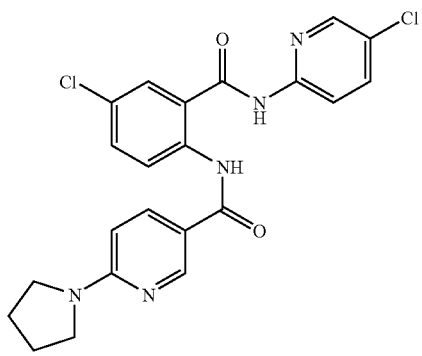

$^1$H-NMR (DMSO-d$_6$) δ 8.64 (d, J=2.3 Hz), 8.46 (d, J=2.3 Hz), 8.34 (d, J=8.7 Hz), 8.14 (d, J=9.0 Hz), 7.99 (d, J=2.6 Hz), 7.96 (d, J=2.6 Hz), 7.95 (d, J=2.6 Hz), 7.92 (d, J=2.3 Hz), 7.62 7.66 (dd, J=9.0 Hz and 2.6 Hz), 6.55 (d, J=9.0 Hz), 3.45 (t, J=6.0 Hz and 5.3 Hz), 1.94-1.99 (m).

ESI-MS, m/e 456.20 (M+1)

Analysis for C$_{22}$H$_{19}$Cl$_2$N$_5$O$_2$:
Calcd: C, 57.91; H, 4.20; N, 15.35.
Found: C, 57.96; H, 4.30; N, 15.14.

EXAMPLE 4

5-Chloro-2-[6-(4-methylpiperazin-1-yl)pyridin-3-ylcarbonyl-amino]-N-(5-chloropyridin-2-yl)benzamide

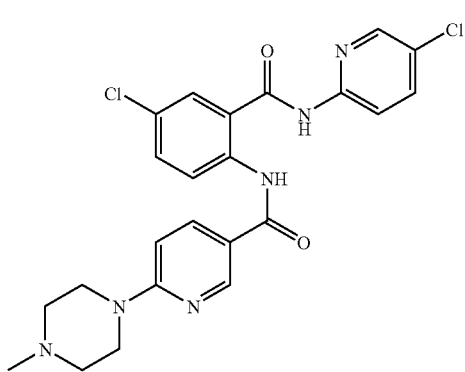

$^1$H-NMR (DMSO-d$_6$) δ 8.65 (d, J=2.6 Hz), 8.45 (d, J=2.3 Hz), 8.28 (d, J=9.0 Hz), 8.13 (d, J=8.7 Hz), 7.93-7.99 (m), 7.66 (d, J=2.3 Hz), 7.62 (d, J=2.6 Hz), 6.93 (d, J=9.-0 Hz), 3.61-3.65 (t, J=4.9 Hz), 2.37-2.40 (t, J=4.9 Hz), 2.21 (s).

ESI-MS, m/e 485.46 (M+1)

EXAMPLE 5

5-Chloro-2-[6-(4-isopropylpiperazin-1-yl)pyridin-3-yl-carbonylamino]-N-(5-chloropyridin-2-yl)benzamide

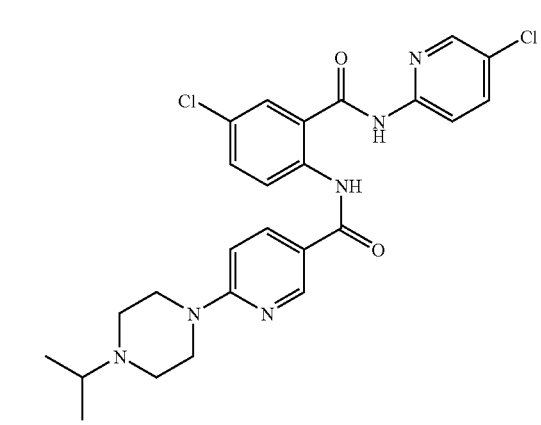

$^1$H-NMR

ESI-MS, m/e 513.45 (M+1)

EXAMPLE 6

5-Chloro-2-[6-(3-hydroxypyrrolidin-1-yl)pyridin-3-yl-carbonylamino]-N-(5chloropyridin-2-yl)benzamide

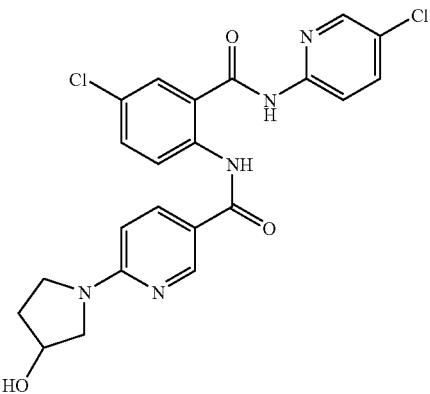

$^1$H-NMR

ESI-MS, m/e 472.21 (M+1)

EXAMPLE 7

5-Chloro-2-[6-(3-hydroxypiperidin-1-yl)pyridin-3-ylcarbonyl-amino]-N-(5-chloropyridin-2-yl)benzamide

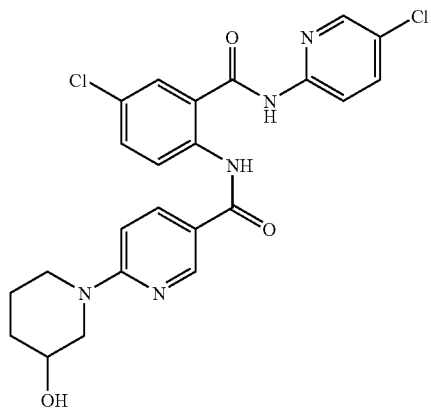

¹H-NMR
ESI-MS, m/e 486.46 (M+1)

EXAMPLE 8

2-[6-(3-Aminopyrrolidin-1-yl)pyridin-3-ylcarbonylamino]-5-chloro-N-(5-chloropyridin-2-yl)benzamide

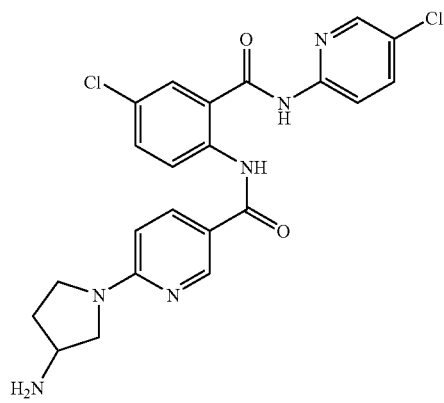

A. 2-[6-(3-t-Butoxycarbonylaminopyrrolidin-1-yl)pyridin-3-ylcarbonylamino]-5-chloro-N-(5-chloropyridin-2-yl)benzamide

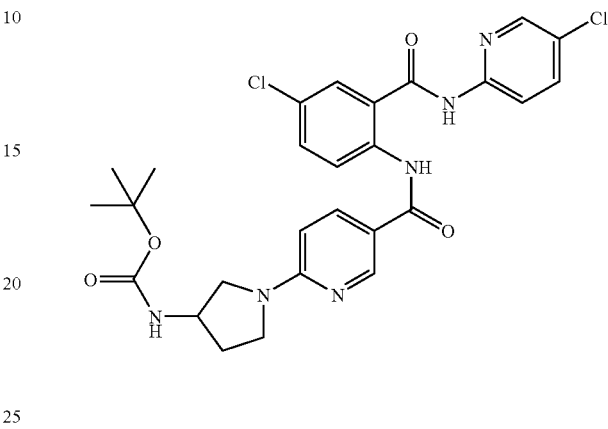

¹H-NMR
ESI-MS, m/e 571.31 (M+1)

B. 2-[6-(3-Aminopyrrolidin-1-yl)pyridin-3-ylcarbonylamino]-5-chloro-N-(5-chloropyridin-2-yl)benzamide

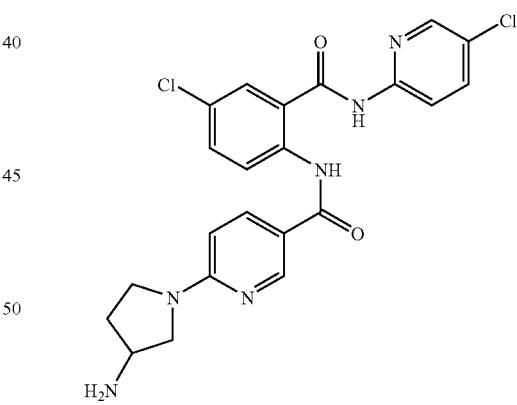

To a solution of the above intermediate (0.140 mg) in methylene chloride (3 mL) was added trifluoroacetic acid (2 mL). The mixture was stirred overnight at room temperature before the solvent was evaporated, and the product was purified using SCX column. Yield=0.120 g ¹H-NMR
ESI-MS, m/e 471.2 (M+1)

EXAMPLE 9

5-Chloro-2-[6-(piperazin-1-yl)pyridin-3-ylcarbonylamino]-N-(5-chloropyridin-2-yl)benzamide

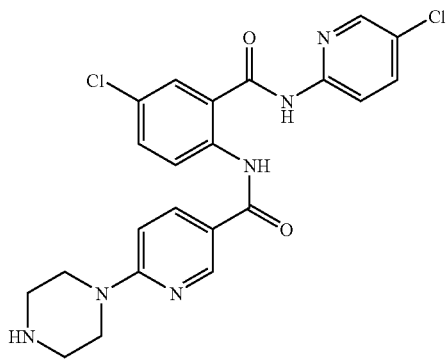

A. 2-[6-(4-t-Butoxycarbonylpiperazin-1-yl)pyridin-3-ylcarbonylamino]-5-chloro-N-(5-chloropyridin-2-yl)benzamide

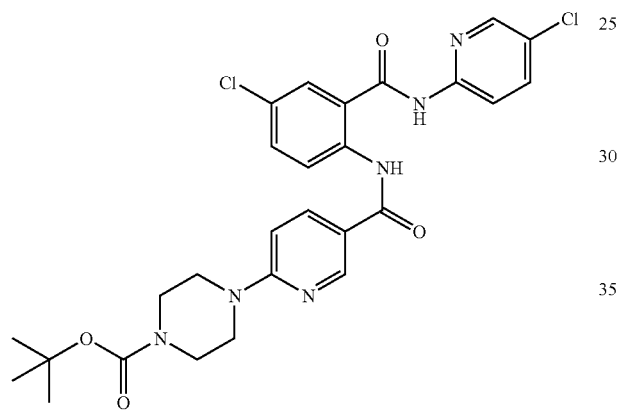

$^1$H-NMR
ESI-MS, m/e 571.23 (M+1).
Analysis for $C_{27}H_{28}Cl_2N_6O_4$:
Calcd: C, 56.75; H, 4.94; N, 14.71.
Found: C, 56.45; H, 4.88; N, 14.34.

B. 5-Chloro-2-[6-(piperazin-1-yl)pyridin-3-ylcarbonylamino]-N-(5-chloropyridin-2-yl)benzamide

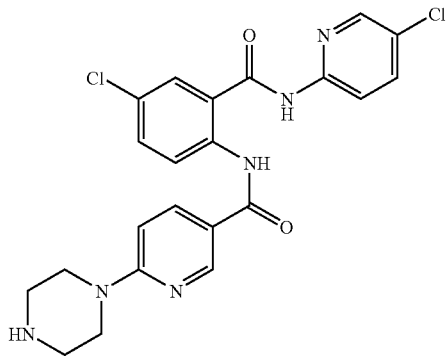

$^1$H-NMR
ESI-MS, m/e 471.14 (M+1).
Analysis for $C_{22}H_{20}Cl_2N_6O_2$:
Calcd: C, 56.06; H, 4.28; N, 17.83.
Found: C, 55.79; H, 4.33; N, 17.63.

EXAMPLE 10

2-[6-(3-Carboxamidopiperidin-1-yl)pyridin-3-ylcarbonyl-amino]-5-chloro-N-(5-chloropyridin-2-yl)benzamide

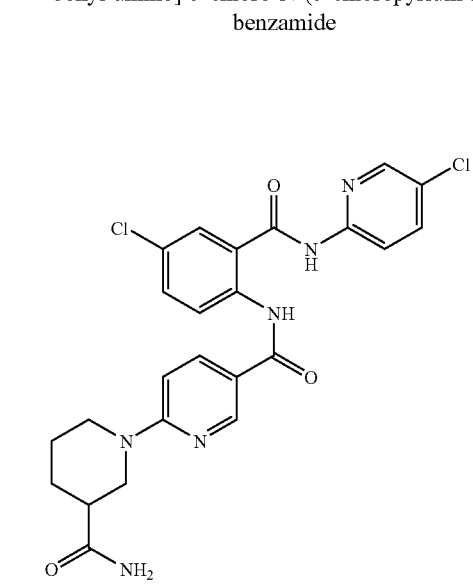

$^1$H-NMR
ESI-MS, m/e 513.31 (M+1).

EXAMPLE 11

5-Chloro-2-[6-(4-formylpiperazin-1-yl)pyridin-3-ylcarbonyl-amino]-N-(5-chloropyridin-2-yl)benzamide

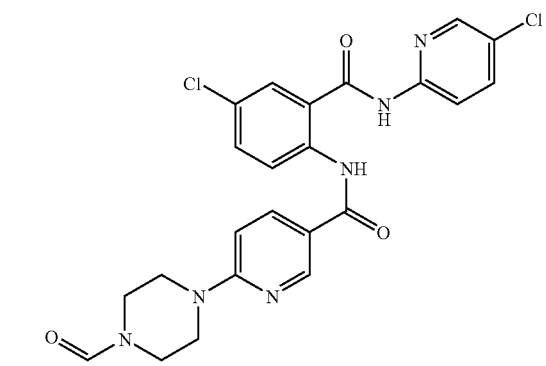

$^1$H-NMR
ESI-MS, m/e 499.24 (M+1).
Analysis for $C_{23}H_{20}Cl_2N_6O_3$:
Calcd: C, 55.32; H, 4.04; N, 16.83.
Found: C, 55.58; H, 4.14; N, 16.49.

EXAMPLE 12

5-Fluoro-2-[6-(3-hydroxymethylpiperidin-1-yl)pyridin-3-yl-carbonylamino]-N-(5-chloropyridin-2-yl)benzamide

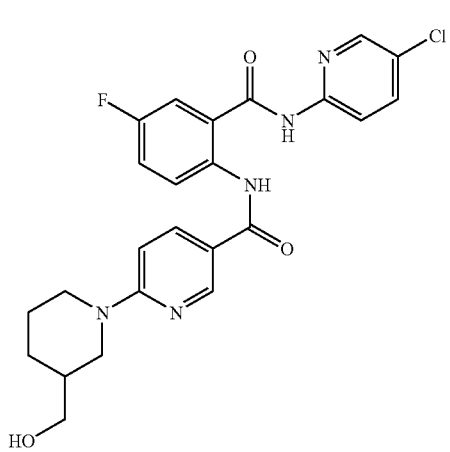

$^1$H-NMR
ESI-MS, m/e 484.44 (M+1).

EXAMPLE 13

5-Fluoro-2-[6-(thiomorpholin-4-yl)pyridin-3-ylcarbonyl-amino]-N-(5-chloropyridin-2-yl)benzamide

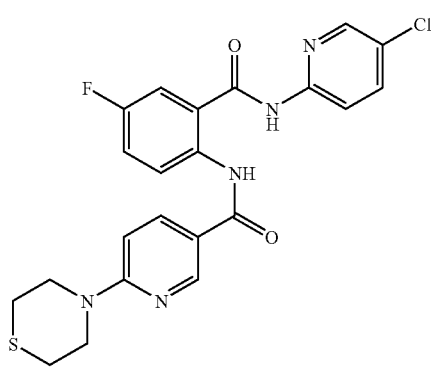

$^1$H-NMR
ESI-MS, m/e 472.22 (M+1)

EXAMPLE 14

5-Chloro-2-[6-(hexahydro-2-oxoazepin-3-ylamino)pyridin-3-ylcarbonylamino]-N-(5-chloropyridin-2-yl)benzamide

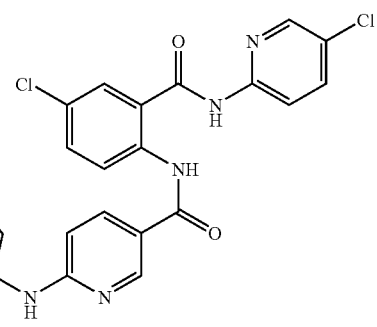

$^1$H-NMR
ESI-MS, m/e 513.42 (M+1).
Analysis for $C_{24}H_{22}Cl_2N_6O_3$:
Calcd: C, 56.15; H, 4.32; N, 16.37.
Found: C, 56.04; H, 4.57; N, 16.15.

EXAMPLE 15

5-Chloro-2-[6-[4-(2-hydroxyethyl)piperazin-1-yl]pyridin-3-ylcarbonylamino]-N-(5-chloropyridin-2-yl)benzamide

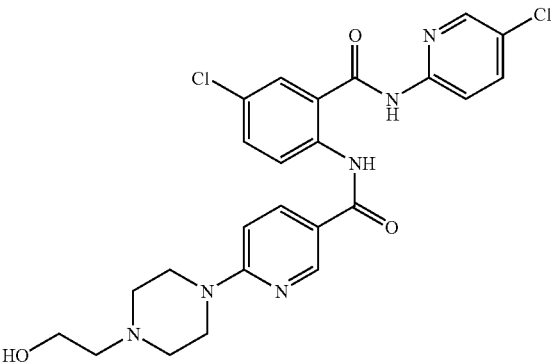

$^1$H-NMR
ESI-MS, m/e 515.31 (M+1).
Analysis for $C_{24}H_{24}Cl_2N_6O_3$:
Calcd: C, 55.93; H, 4.69; N, 16.31.
Found: C, 56.06; H, 4.66; N, 16.38.

EXAMPLE 16

2-[6-(1-Azabicyclo[2.2.2]oct-3-ylamino)pyridin-3-ylcarbonyl-amino]-5-chloro-N-(5-chloropyridin-2-yl)benzamide

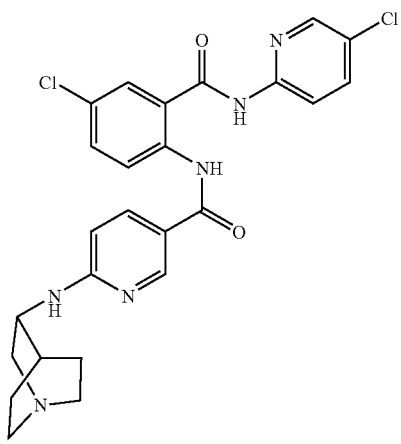

$^1$H-NMR
ESI-MS, m/e 511.56 (M+1).

EXAMPLE 17

5-Chloro-2-[6-(3-oxopiperazin-1-yl)pyridazin-3-ylcarbonyl-amino]-N-(5-chloropyridin-2-yl)benzamide Hydrate.

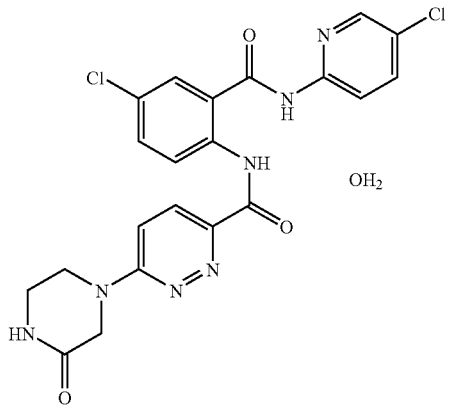

$^1$H-NMR
ESI-MS, m/e 486.01 (M+1).
Analysis for $C_{21}H_{17}Cl_2N_7O_3$:
Calcd: C, 50.01; H, 3.80; N, 19.44.
Found: C, 49.77; H, 3.38; N, 19.16.

EXAMPLE 18

5-Chloro-2-[6-(3-oxopiperazin-1-yl)pyridazin-3-ylcarbonyl-amino]-N-(5-methylpyridin-2-yl)benzamide Hydrate

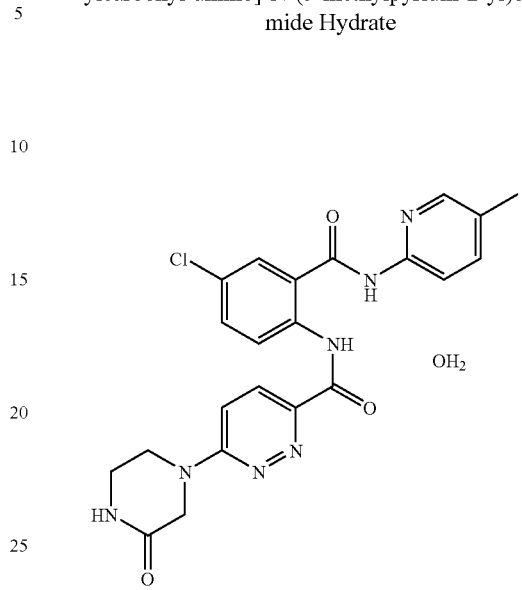

$^1$H-NMR
ESI-MS, m/e 466.1 (M+1).

EXAMPLE 19

5-Chloro-2-[5-(3-hydroxypyrrolidin-1-yl)pyrazin-2-yl-carbonylamino]-N-(5-chloropyridin-2-yl)benzamide

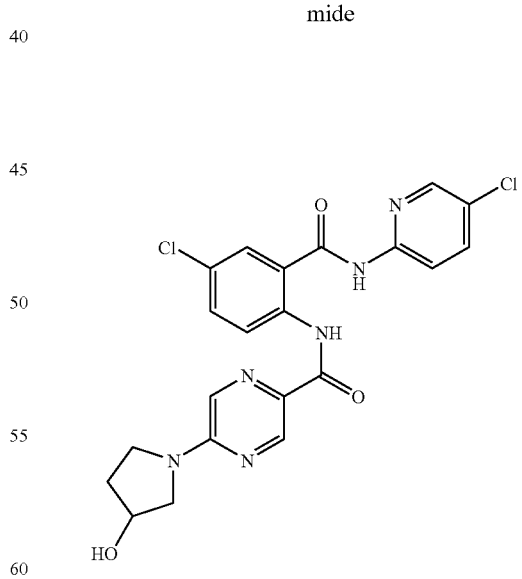

$^1$H-NMR
ESI-MS, m/e 473.11 (M+1).

EXAMPLE 20

2-[2-(3-Aminopyrrolidin-1-yl)pyrazin-2-ylcarbonylamino]-5-chloro-N-(5-chloropyridin-2-yl)benzamide

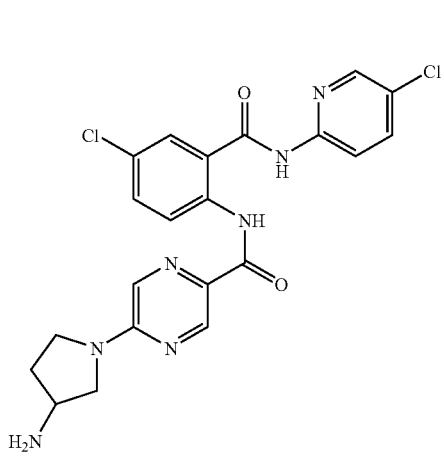

A. 2-[5-(3-t-Butoxycarbonylaminopyrrolidin-1-yl)pyrazin-2-ylcarbonylamino]-5-chloro-N-(5-chloropyridin-2-yl)benzamide

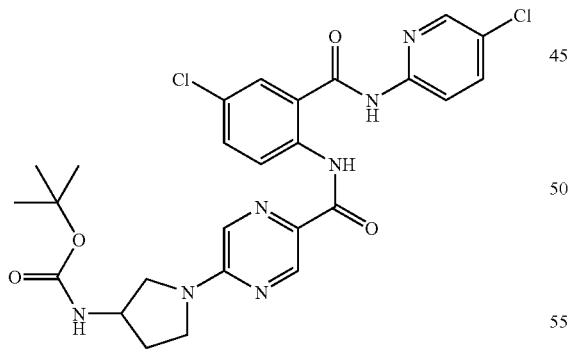

$^1$H-NMR
ESI-MS, m/e 571.1 (M+).
Analysis for $C_{26}H_{27}Cl_2N_7O_4$:
Calcd: C, 54.55; H, 4.75; N, 17.13.
Found: C, 54.78; H, 4.80; N, 16.87.

B. 2-[2-(3-Aminopyrrolidin-1-yl)pyrazin-2-ylcarbonyl-amino]-5-chloro-N-(5-chloropyridin-2-yl)benzamide

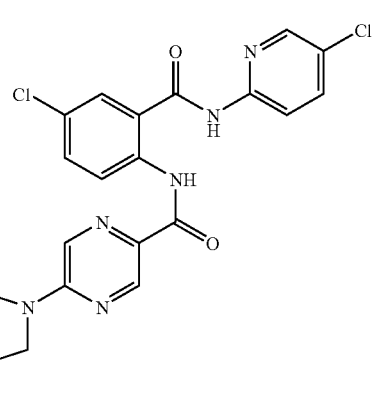

$^1$H-NMR
ESI-MS, m/e 472.2 (M+1).

EXAMPLE 21

5-Chloro-2-[5-(piperazin-1-yl)pyrazin-2-ylcarbonylamino]-N-(5-chloropyridin-2-yl)benzamide

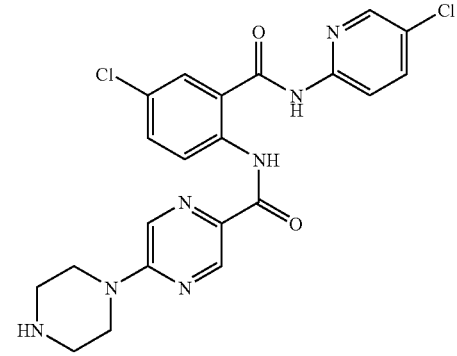

57

A. 2-[5-(4-t-Butoxycarbonylpiperazin-1-yl)pyrazin-2-yl-carbonylamino]-5-chloro-N-(5-chloropyridin-2-yl)benzamide

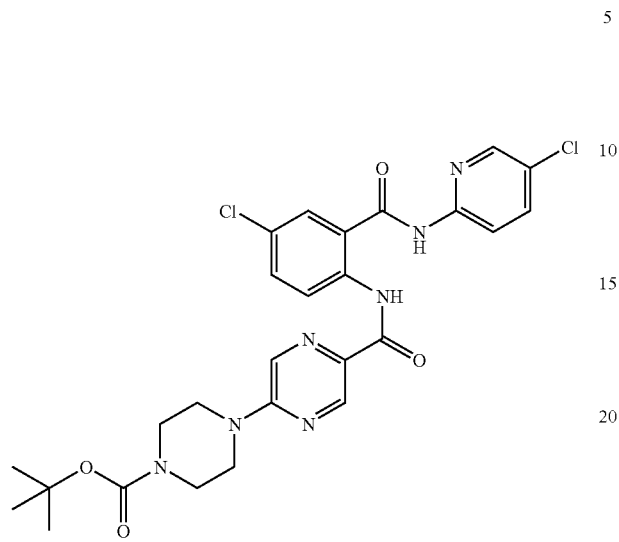

$^1$H-NMR
ESI-MS, m/e 571.96 (M+1).

B. 5-Chloro-2-[5-(piperazin-1-yl)pyrazin-2-ylcarbonyl-amino]-N-(5-chloropyridin-2-yl)benzamide

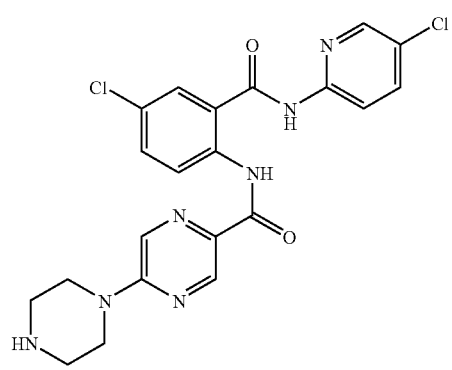

$^1$H-NMR
ESI-MS, m/e 472.44 (M+1).
Analysis for $C_{21}H_{19}Cl_2N_7O_2$:
Calcd: C, 53.40; H, 4.05; N, 20.76.
Found: C, 53.30; H, 3.96; N, 20.51.

58

EXAMPLE 22

5-Chloro-2-[5-(piperazin-1-yl)pyrazin-2-ylcarbonylamino]-N-(5-methylpyridin-2-yl)benzamide

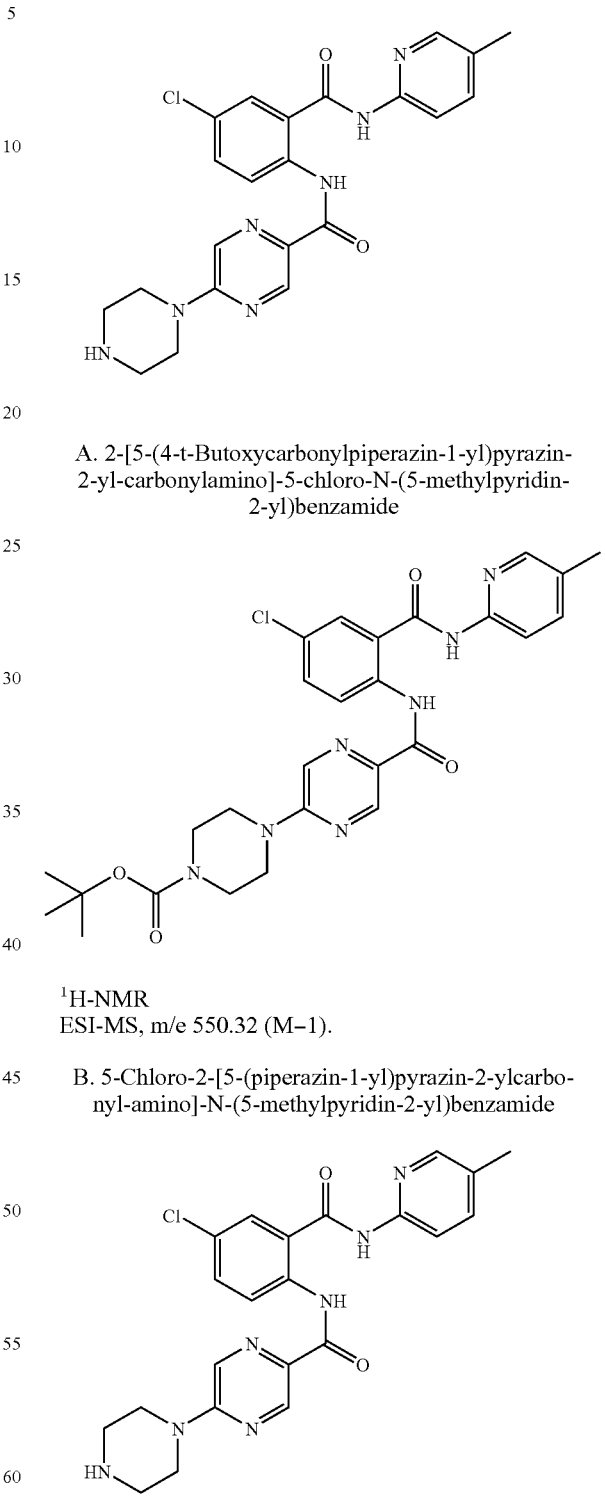

A. 2-[5-(4-t-Butoxycarbonylpiperazin-1-yl)pyrazin-2-yl-carbonylamino]-5-chloro-N-(5-methylpyridin-2-yl)benzamide $^1$H-NMR
ESI-MS, m/e 550.32 (M−1).

B. 5-Chloro-2-[5-(piperazin-1-yl)pyrazin-2-ylcarbonyl-amino]-N-(5-methylpyridin-2-yl)benzamide $^1$H-NMR
ESI-MS, m/e 449.99 (M−1).
Analysis for $C_{22}H_{22}ClN_7O_2$:
Calcd: C, 58.47; H, 4.91; N, 21.70.
Found: C, 58.56; H, 4.62; N, 21.57.

EXAMPLE 23

Preparation of 5-Fluoro-2-[(5-methylthiopyridin-2-yl)-carbonylamino]-N-(5-chloropyridin-2-yl)benzamide

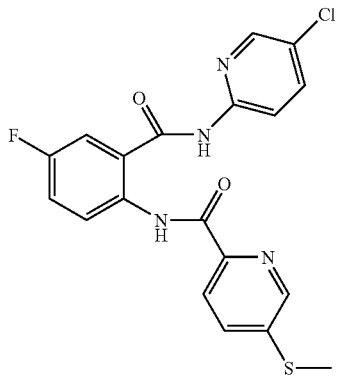

A mixture of 5-fluoro-2-[(5-fluoropyridin-2-yl)-carbonylamino]-N-(5-chloropyridin-2-yl)benzamide (502 mg, 1.29 mmol), DMSO (4 mL) and sodium thiomethoxide (95 mg, 1.36 mmoL) was heated to 50° C. for 18 h. The reaction was cooled, added water, filtered, and dried. The solid was triturated with $CH_2Cl_2$ and filtered to give the title compound as a white solid (461 mg, 86%).

$^1$H-NMR (300 MHz, DMSO-$d_6$): δ 2.61 (s, 3H), 7.49 (m, 1H), 7.78 (dd, J=2.9, 9.5 Hz, 1H), 7.90 (dd, J=2.2, 9.5 Hz, 1H), 8.05 (m, 2H), 8.15 (d, J=9.5 Hz, 1H), 8.47 (d, J=2.2 Hz, 1H), 8.60 (m, 2H), 11.28 (s, 1H), 12.03 (s, 1H).

ES-MS, exact m/e for $[C_{19}H_{15}ClFN_4O_2S+H]$: Calc: 417.0588; Found: 417.0577.

EXAMPLE 24

Preparation of 5-Fluoro-2-[(5-methylsulfinylpyridin-2-yl)-carbonylamino]-N-(5-chloropyridin-2-yl)benzamide

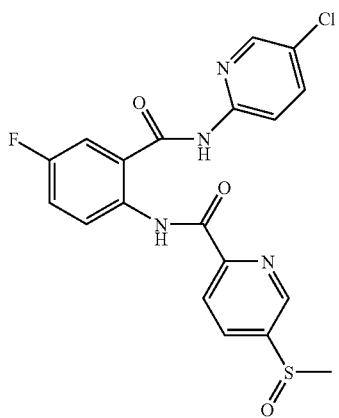

To a 0° C. mixture of 5-fluoro-2-[(5-methylthiopyridin-2-yl)carbonylamino]-N-(5-chloropyridin-2-yl)benzainide (450 mg, 1.08 mmol) in acetone (20 mL) was added 50% 3-choloroperbenzoic acid (838 mg, 2.43 mmol). The reaction was stirred for 30 minutes at 0° C., quenched with satd $NaHSO_3$, and warmed to room temperature. The mixture was extracted with EtOAc. The organic layer was washed with 50% satd $Na_2CO_3$, and the resulting product precipitate was filtered. The filtrate was partitioned and the organic layer was combined with the product precipitate. This mixture was concentrated and dissolved in acetone, for adsorption onto silica gel, there was added 1.2 g silica gel and the mixture was concentrated. The resulting solid was chromatographed on silica gel ($CH_2CL_2$ to 20% $EtOAc/CH_2Cl_2$) and the concentrated product was triturated with EtOAc to afford the title compound as a white solid (226 mg, 48%).

$^1$H-MMR (300 MHz, DMSO-$d_6$): δ 2.92 (s, 3H), 7.53 (dt, J=2.2, 5.9 Hz, 1H), 7.81 (dd, J=2.9, 9.5 Hz, 1H), 8.02 (dd, J=2.9, 9.1 Hz, 1H), 8.16 (d, J=8.8 Hz, 1H), 8.36 (m, 2H), 8.47 (d. J=2.2 Hz, 1H), 8.60 (dd, J=5.1, 9.1 Hz, 1H), 8.98 (s, 1H), 11.32 (br s, 1H), 12.19 (br s, 1H).

ES-MS, exact m/e for $[C_{19}H_{15}ClFN_4O_3S+H]$: Calc: 433.5037; Found: 433.5027.

EXAMPLE 25

Preparation of 5-Fluoro-2-[(5-methylthiopyrimidin-2-yl)-carbonylamino]-N-(5-chloropyridin-2-yl)benzamide

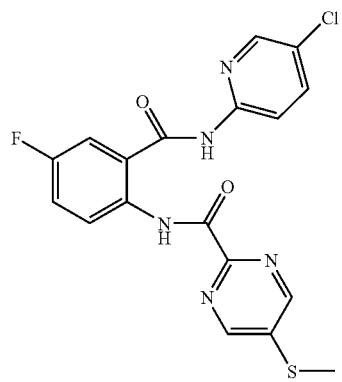

Using a similar procedure to that of Example 23, 5-fluoro-2-[5-fluoropyrimidin-2-ylcarbonylamino]-N-(5-chloropyridin-2-yl)benzamide gave the title compound as a white solid (53 mg, 55%).

$^1$H-NMR (300 MHz, DMSO-$d_6$): δ 2.67 (s, 3H), 7.52 (m, 1H), 7.82 (dd, J=2.9, 9.5 Hz, 1H), 8.01 (dd, J=2.9, 11.7 Hz, 1H), 8.13 (d, J=8.8 Hz, 1H), 8.47 (d, J=2.2 Hz, 1H), 8.61 (dd, J=5.5, 9.1 Hz, 1H), 8.90 (s, 2H), 11.3 (br s, 1H), 12.25 (br s, 1H)

ES-MS, exact m/e for $[C_{18}H_{14}ClFN_5O_2S+H]$: Calc: 418.0541; Found: 418.0563.

EXAMPLE 26

5-Fluoro-2-[(5-methoxypyrimidin-2-yl)carbonylamino]-N-(5-fluoropyridin-2-yl)benzamide

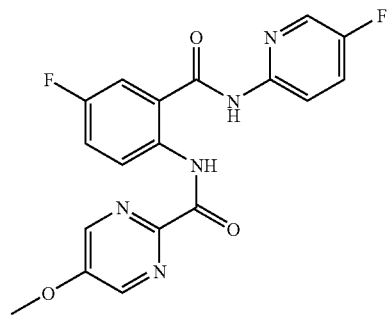

The title compound was obtained as a by-product in the preparation of 5-fluoro-2-(5-fluoropyrimidin-2-ylcarbonyl-amino}-N-(5-fluoropyridin-2-yl)benzamide (Intermediate C-1, above). Conveniently, the title compound may be obtained from Intermediate C-1 using a procedure similar to that of Example 23, above, but using sodium methoxide instead of sodium thiomethoxide.

$^1$H-NMR

ESI-MS, m/e 384.2 (M−1).

What is claimed is:

1. A compound of formula I,

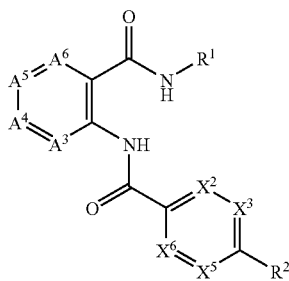

or a pharmaceutically acceptable salt thereof, wherein
$A^3$, $A^4$, $A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$; wherein
each of $R^3$, $R^4$ and $R^6$ is hydrogen; and $R^5$ is fluoro or chloro;
$R^1$ is 2-pyridinyl which bears a fluoro or chloro substituent at the 5-position;
$X^2$ is N and each of $X^3$, $X^5$ and $X^6$ is CH; or
$X^3$ is N and each of $X^2$, $X^5$ and $X^6$ is CH; and
$R^2$ is —$NR^sR^t$ in which $R^s$ is hydrogen and $R^t$ is hexahydro-2-oxoazepin-3-yl or 1-azabicyclo[2.2.2]oct-3-yl, or —$NR^sR^t$ is pyrrolidin-1yl, 3-aminopyrrolidin-1-yl, 3-hydroxypyrrolidin-1-yl, 3-aminocarbonylpiperidin-1-yl, 3-hydroxypiperidin-1-yl, 3-hydroxymethylpiperidin-1-yl, morpholin-4-yl, thiomorpholin-4-yl, piperazin-1-yl, 4-methylpiperazin-1-yl, 4-isopropylpiperazin-1-yl, 4-formyl-piperazin-1-yl, 4-(2-hydroxyethyl)piperazin-1-yl, or 3-oxopiperazin-1-yl.

2. The compound, or salt thereof, of claim 1 wherein —$NR^sR^t$ is pyrrolidin1yl, 3-aminopyrrolidin-1-yl, 3hydroxypyrrolidin-1yl, 3-hydroxypiperidin-1-yl, morpholin-4-yl, 4-methylpiperazin-1-yl or 4-isopropylpiperazin-1-yl.

3. The compound, or salt thereof, of claim 2 wherein —$NR^sR^t$ is 3-aminopyrrolidin-1-yl or 3-hydroxyl-pyrrolidin-1-yl.

4. The compound of claim 1 which is selected from
a. 5-chloro-2-[6-(3-hydroxypyrrolidin-1-yl)pyridin-3-yl-carbonylamino]-N-(5-chloropyridin-2-yl)benzamide, and
b. 2-[6-(3-aminopyrrolidin-1-yl)pyridin-3ylcarbonyl-amino]-5-chloro-N-(5chloropyridin-2-yl)benzamide;
or a pharmaceutically acceptable salt thereof.

5. The pharmaceutically acceptable salt of claim 1 which is the acid addition salt of a basic compound of formula I with an inorganic or organic acid which affords a physiologically acceptable anion.

6. A pharmaceutical composition comprising in association with a pharmaceutically acceptable carrier, diluent or excipient, a compound of formula I, or a pharmaceutically acceptable salt thereof, as provided in claim 1.

7. A process for preparing a compound of formula I, or a pharmaceutically acceptable salt thereof, as provided in claim 1, wherein a functional group of an amino of formula H—$NR^sR^t$, which is not involved in the indicated process may be in a form in which the functional group is protected using a protecting group, which comprises:
for a compound of formula I in which $R^2$ is-$NR^sR^t$, substituting the group $Y^a$ of a compound of formula II,

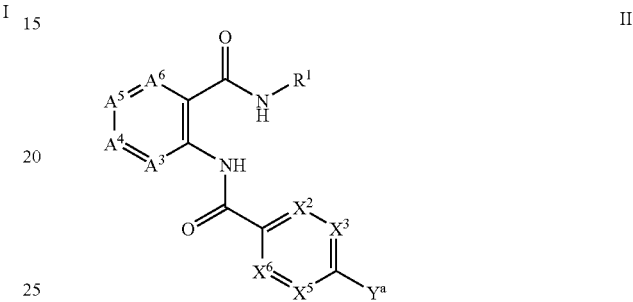

in which $Y^a$ is a leaving group for nucleophilic aromatic substitution, using an amine of formula H—$NR^sR^t$; whereafter, when the functional group is protected using a protecting group, removing the protecting group; whereafter, when a pharmaceutically acceptable salt of a compound of formula I is required, it is obtained by reacting the basic form of a basic compound of formula I with an acid affording a physiologically acceptable counterion or by any other conventional procedure, and wherein, unless otherwise specified, $A^3$-$A^6$, $R^1$—$R^2$, $X^2$—$X^3$ and $X^5$—$X^6$ have any of the values defined in claim 1.

8. An acid of formula IV,

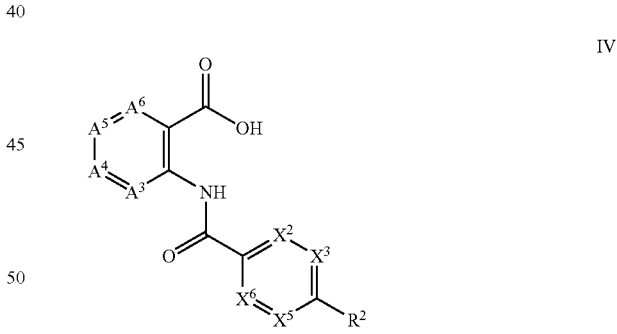

or an activated derivative thereof, or a salt of the acid or activated derivative, in which $A^3$-$A^6$, $X^2$—$X^3$, $X^5$—$X^6$ have any of the values defined in Claim 1, and $R^2$ is —$NR^sR^t$ wherein —$NR^sR^t$ is 3-aminopyrrolidin-1-yl or 3-hydroxy-pyrrolidin1-yl; or a derivative thereof in which a functional group other than the carboxy group, or activated derivative thereof, is protected using a protecting group.

9. A method of inhibiting coagulation in a mammal comprising administering to a mammal in need of treatment, a coagulation inhibiting dose of a compound of formula I, or a pharmaceutically acceptable salt thereof, as described in claim 1.

10. A process for preparing a compound of formula I, or a pharmaceutically acceptable salt thereof, as provided in claim 1, wherein a functional group of $R^2$ of formula IV, which is not involved in the indicated process may be in a form in which the functional group is protected using a protecting group which comprises:

acylating an amine of formula $H_2N—R^1$, or a deprotonated derivative thereof, using an acid of formula IV or an activated derivative thereof, whereafter, when the functional group is protected using a protecting group, removing the protecting group; whereafter, when a pharmaceutically acceptable salt of a compound of formula I is required, it is obtained by reacting the basic form of a basic compound of formula I with an acid affording a physiologically acceptable counterion or by any other conventional procedure, and wherein, unless otherwise specified, $A^3$-$A^6$, $R^1$—$R^2$, $X^2$—$X^3$ and $X^5$-$X^6$ have any of the values defined in claim 1.

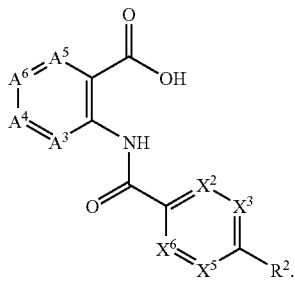

IV

11. A process for preparing a compound of formula I, or a pharmaceutically acceptable salt thereof, as provided in claim 1, wherein a functional group of R2 of formula VII, which is not involved in the indicated process may be in a form in which the functional group is protected using a protecting group, which comprises: acylating an amine of formula VI,

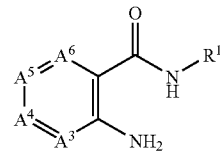

VI using an acid of formula VII, using an acid of formula

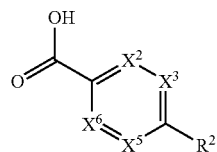

VII or an activated derivative thereof, whereafter, when the functional group is protected using a protecting group, removing the protecting group; whereafter, when a pharmaceutically acceptable salt of a compound of formula I is required, it is obtained by reacting the basic form of a basic compound of formula I with an acid affording a physiologically acceptable counterion or by any other conventional procedure, and wherein, unless otherwise specified, $A^3$-$A^6$, $R^1$—$R^2$, $X^2$—$X^3$ and $X^5$—$X^6$ have any of the values defined in claim 1.

* * * * *